(12) United States Patent
Amemiya et al.

(10) Patent No.: US 7,053,376 B2
(45) Date of Patent: May 30, 2006

(54) RADIOLOGICAL IMAGING APPARATUS AND RADIOLOGICAL IMAGING METHOD AND RADIOLOGICAL IMAGING SUPPORT METHOD

(75) Inventors: Kensuke Amemiya, Hitachinaka (JP); Yuuichirou Ueno, Hitachi (JP); Hiroshi Kitaguchi, Naka (JP); Kikuo Umegaki, Hitachinaka (JP); Shinichi Kojima, Hitachi (JP); Norihito Yanagida, Hitachi (JP); Kazuma Yokoi, Hitachi (JP); Takashi Okazaki, Hitachinaka (JP)

(73) Assignee: Hitachi, Ltd., Tokyo (JP)

( * ) Notice: Subject to any disclaimer, the term of this patent is extended or adjusted under 35 U.S.C. 154(b) by 56 days.

(21) Appl. No.: 10/246,450

(22) Filed: Sep. 19, 2002

(65) Prior Publication Data

US 2003/0179853 A1  Sep. 25, 2003

(30) Foreign Application Priority Data

Mar. 20, 2002 (JP) ............................... 2002-077464
Mar. 28, 2002 (JP) ............................... 2002-090200

(51) Int. Cl.
*G01T 1/166* (2006.01)

(52) U.S. Cl. .................. 250/363.04; 378/4; 378/19
(58) Field of Classification Search ............ 378/4–20, 378/63; 250/363.03, 363.04
See application file for complete search history.

(56) References Cited

U.S. PATENT DOCUMENTS

| 5,125,012 A | 6/1992 | Schittenhelm |
| RE34,160 E | 1/1993 | Fetter |
| 5,210,421 A | 5/1993 | Gullberg et al. |
| 6,310,968 B1 | 10/2001 | Hawkins et al. |
| 6,448,559 B1 * | 9/2002 | Saoudi et al. ............ 250/367 |

FOREIGN PATENT DOCUMENTS

| JP | 4-263839 | 9/1992 |
| JP | 5-302979 | 11/1993 |
| JP | 7-20245 | 1/1995 |
| JP | 9-5441 | 1/1997 |
| JP | 2000-107162 | 4/2000 |
| JP | 2000-180550 | 6/2000 |
| JP | 2001-17420 | 1/2001 |

OTHER PUBLICATIONS

Shepp et al., "Reconstructing Interior Head Tissue from X–Ray Transmissions", IEEE Transactions on Nuclear Science, vol. NS–21, No. 1, Feb. 1974, pp. 228–229, The Institute of Electrical and Electronics Engineers, Inc., New York, NY.

* cited by examiner

*Primary Examiner*—Craig E. Church
*Assistant Examiner*—Jurie Yun
(74) *Attorney, Agent, or Firm*—Dickstein Shapiro Morin & Oshinsky LLP

(57) ABSTRACT

A radiological imaging apparatus of the present invention includes an X-ray source for emitting an X-ray, a γ-ray detecting section for outputting a detection signal of a γ-ray, and an X-ray detecting section for outputting a detecting signal of an X-ray. The X-ray source moves around a bed for placing an examinee. The γ-ray detecting section has a plurality of radiation detectors aligned in the longitudinal direction of the bed and placed around the bed. The X-ray detecting section is positioned in a region formed between one end and the other end of the γ-ray detecting section in the longitudinal direction of the bed. The X-ray source is also positioned in the region. Since the X-ray detecting section is placed in the region, it is possible to accurately combine a PET image and an X-ray computed tomographic image.

33 Claims, 12 Drawing Sheets

RADIOLOGICAL IMAGING APPARATUS AND RADIOLOGICAL IMAGING METHOD AND RADIOLOGICAL IMAGING SUPPORT METHOD

BACKGROUND OF THE INVENTION

The present invention relates to a radiological imaging apparatus and radiological imaging method, and more particularly, to a radiological imaging apparatus and radiological imaging method ideally applicable to perform radiological imaging using X-ray computed tomography and positron emission computed tomography (hereinafter referred to as "PET") and to perform radiological imaging using X-ray computed tomography and single photon emission computed tomography (hereinafter referred to as "SPECT").

As radiological imaging methods using a human body as a test object, X-ray computed tomography, PET and SPECT, etc. are available. In PET and SPECT, a physical quantity is measured on an integral value (in a flying direction) of radiation emitted from a human body, and back projection of the integral value makes it possible to compute a physical quantity of each voxel in the human body and perform imaging. For such imaging, it is necessary to process an enormous amount of data. Rapid development of computer technology in recent years makes it possible to provide tomography of the human body with high speed and accuracy.

With PET and SPECT, it is possible to detect functions and metabolism at a level of molecular biology that cannot be detected by X-ray computed tomography and so on, and it is possible to provide a function image of the body of a medical examinee.

PET is a method comprising steps administering radiopharmaceutical (hereinafter referred to as "PET radiopharmaceutical") including positron emitters ($^{15}$O, $^{13}$N, $^{11}$C, $^{18}$F, etc., the half life is 2 to 110 minutes) to the examinee and examining locations in the body where more PET radiopharmaceutical are consumed. As an example of the PET radiopharmaceutical, 2-[F-18]fluoro-2-deoxy-D-glucose, $^{18}$FDG is available. Since $^{18}$FDG highly concentrates on tumor tissue due to carbohydratemetabolism, $^{18}$FDG is used for identifying a tumor. One positron is emitted from a positron emitter contained in the PET radiopharmaceutical concentrating on a specific point, and the positron couples with an electron of a neighboring cell to disappear and irradiates a pair of γ-rays having energy of 511 keV. These γ-rays are emitted in directions substantially opposite to each other (180°±0.6°). Detecting this pair of γ-rays (referred to as a γ-ray pair) using a radiation detector makes it possible to know between which radiation detectors the positron is emitted. Detecting many γ-ray pairs makes it possible to identify locations where more PET radiopharmaceutical are consumed. For example, as described above, since $^{18}$FDG highly concentrates on cancer cells having hyperactive carbohydrate metabolism. Thus, it is possible to discover cancer focuses using PET. The obtained data is converted to radiation density of each voxel using filtered back projection method, which is described IEEE Transactions on Nuclear Science, NS-21, pages 228 to 229, and the data contributes to imaging of locations of γ-rays (locations where a radionuclide concentrates, that is, a location of a cancer cell).

In SPECT, radiopharmaceutical (hereinafter referred to as "SPECT radiopharmaceutical") containing a matter having a property of concentrating on a specific tumor or molecule and single photon emitters ($^{99}$Tc, $^{67}$Ga, $^{201}$Tl, etc.) is administered to an examinee, and γ-rays emitted from the nuclides of the body are detected using a γ-ray detector. The energy of γ-rays emitted from the single photon emitters is around several 100 keV. Since the SPECT radiopharmaceutical concentrates on an area affected by cancer, it is possible to identify the cancer area. In the case of the SPECT as well, obtained data is converted to data of each voxel using a method such as filtered back projection. Besides, a transmission image is often taken in SPECT as well. $^{99}$Tc, $^{67}$Ga and $^{201}$Tl have a half life longer than that of radioisotopes used for the PET, for example, 6 hours to 3 days.

As described above, in the PET and SPECT, since a function image is obtained using internal metabolism, a part where radiopharmaceutical concentrates can be extracted with high contrast. However, it is not possible to know the position from adjacent organs. Thus, in recent years, the following technology has received attention: a conformation image as a tomographic image obtained by X-ray computed tomography is combined with a function image as a tomographic image obtained by the PET or SPECT to perform a high degree of diagnosis. As an example of the technology, technology described in JP-A-7-20245 is available.

In a radiological imaging apparatus of JP-A-7-20245, an X-ray computed tomography imaging apparatus and a PET imaging apparatus are placed in series, a bed where the examinee is laid down is moved horizontally, and examination is carried out on the examinee using the imaging apparatuses. Namely, an X-ray computed tomographic examination is carried out on the examinee using the X-ray computed tomography imaging apparatus, and then, a PET examination is performed on the examinee using the PET imaging apparatus. PET data and X-ray computed tomographic data which are the image data obtained by the two imaging apparatuses are combined to identify the focus location of the examinee.

JP-A-9-5441 describes a radiological imaging apparatus which also serves as a bed with an X-ray computed tomography imaging apparatus and a SPECT imaging apparatus placed in series. X-ray computed tomographic data and SPECT data which are the image data obtained by those imaging apparatuses are combined to identify the focus location of the examinee.

In the radiological imaging apparatuses of the above publications, the two different examinations are carried out with shifted positions. Thus, the examinations inevitably have a time lag.

SUMMARY OF THE INVENTION

The present invention has as its object the provision of a radiological imaging apparatus and a radiological imaging method that can improve accuracy of diagnosis.

A first invention for attaining the above object is characterized in that at least part of an X-ray detecting section is positioned in a region formed between one end and the other end of a γ-ray detecting section in the longitudinal direction of a bed. The X-ray detection section outputs X-ray detection signals, and the γ-ray detecting section outputs γ-ray detection signals.

In the first invention, since at least part of the X-ray detecting section is positioned in the region, even when a test object moves during an in examination not by movement of the bed, it is possible to improve accuracy of a tomographic image of the test object created by first information and second information. The first information is obtained from γ-ray detection signals outputted from the γ-ray detecting section, and the second information is obtained from X-ray detection signals outputted from the X-ray detecting section. Using the tomographic image, it is possible to improve accuracy of diagnosis on the test object. To be specific, it is possible to accurately recognize the position and the size of a cancer. Particularly it is possible to accurately perform diagnosis on a cancer of lymph gland, which is an organelle.

To be specific, the created tomographic image is provided by combining first tomographic image information (for example, including an image of a part on which radiopharmaceutical concentrates), which is produced by the first information, and second tomographic image information (for example, including an image of bones), which is produced by the second information. Since at least part of the X-ray detecting section is positioned in the region, the first tomographic image information and the second tomographic image information be combined with accuracy, thereby improving accuracy of a tomographic image.

It is preferable that the γ-ray detecting section and the X-ray detecting section are integrated to constitute a radiation detecting section serving as the γ-ray detecting section and the X-ray detecting section, and the radiation detecting section is constituted by radiation detectors for outputting both of the a γ-ray detection signal and an X-ray detection signal. With this configuration, it is not necessary to separately provide the γ-ray detecting section and the X-ray detecting section, and the radiation detecting section having both functions of the γ-ray detecting section and the X-ray detecting section is formed. The radiation detecting section outputs both of the γ-ray detection signal and the X-ray detection signal. Thus, the radiation imaging apparatus becomes compact.

A second invention for attaining the above objective is characterized by comprising a γ-ray detecting section which is positioned around a bed, detects a γ-ray, and outputs a γ-ray detection signal, and an X-ray detecting section which detects an X-ray and outputs a detection signal of the X-ray at the position for detecting a γ-ray. Since the X-ray detecting section is provided for detecting an X-ray and outputs a detection signal of the X-ray at the position for detecting a γ-ray, even when a test object moves during an examination not by movement of the bed, it is possible to obtain an accurate tomographic image as in the case of the first invention. Thus, it is possible to improve accuracy of diagnosis on the test object.

A third invention for attaining the above objective is characterized by comprising a γ-ray detecting section which detects a γ-ray emitted from a test object at the position of the test object irradiated with X-rays and outputs a detection signal of the γ-ray. The third invention also makes it possible to obtain an accurate tomographic image as in the case of the first invention even when the test object moves during an examination not by movement of a bed.

A fourth invention for attaining the above objective is characterized in that a radiation detector for detecting a γ-ray irradiated from a test object detects an X-ray passing through the test object, and the radiological imaging apparatus comprises signal processing apparatus for inputted a γ-ray detection signal and an X-ray detection signal which are outputted from the radiation detector. Since the radiation detector for detecting a γ-ray detects an X-ray, the fourth invention also makes it possible to improve accuracy of diagnosis on the test object as in the case of the first invention and to achieve a compact radiological imaging apparatus.

A fifth invention for attaining the above objective is characterized by comprising an X-ray source positioned in a region formed between one end and the other end of a γ-ray detecting section in the longitudinal direction, and an X-ray detecting section for outputting a detection signal of an X-ray. Since the fifth invention has the X-ray source positioned in the region, X-rays are irradiated on the test object, and γ-rays emitted from the test object can be detected in the γ-ray detecting section. Hence, even when a test object moves during an examination not by movement of the bed, it is possible to obtain an accurate tomographic image as in the case of the first invention.

A sixth invention for attaining the above objective is characterized by comprising a plurality of gaps formed at intervals in the longitudinal direction of a bed, a γ-ray detecting section for outputting a detection signal of a γ-ray, an X-ray detecting section for outputting a detection signal of an X-ray, an X-ray source for irradiating X-rays onto a test object through the gaps, and an X-ray source transfer apparatus for moving the X-ray source in the longitudinal direction. In the sixth invention, X-rays passing through the gaps formed on the γ-ray detecting section can be irradiated onto the test object, X-rays passing through the test object can be detected in the X-ray detecting section, and γ-rays can be detected in the γ-ray detecting section. Thus, it is possible to improve accuracy of diagnosis on the test object as in the case of the first invention. Since the X-ray source can move in the longitudinal direction of the bed, both of an X-ray detecting examination and a γ-ray detecting examination can be performed on the test object without moving the examinee in the longitudinal direction of the bed.

A seventh invention for attaining the above objective is characterized by comprising a γ-ray detecting device and an X-ray detecting device detachably attached to the γ-ray detecting device. The γ-ray detecting device has a γ-ray detecting section for outputting a detection signal of a γ-ray, and the X-ray detecting device has an X-ray detecting section for outputting a detection signal of an X-ray, an X-ray source for irradiating X-rays onto a test object through gaps formed on the γ-ray detecting section, and an X-ray source transfer apparatus for moving the X-ray source in the longitudinal direction of a bed. The seventh invention can obtain the effect of the sixth invention and can separate the X-ray detecting device from the γ-ray detecting device, thereby performing an examination of X-ray detection using the X-ray detecting device.

An eighth invention is characterized by comprising an image pickup apparatus and a controller. The controller performs control such that a plurality of radiation detectors and a power supply are connected to apply voltage to the plurality of radiation detectors, X-rays are emitted from the x-ray source when a set time elapses from the application of voltage to the radiation detector, and the X-ray source which has emitted the X-rays is moved in the circumferential direction using the first X-ray source transfer apparatus. According to the eighth invention, since voltage is applied to the plurality of radiation detectors and X-rays are emitted from the X-ray source when the set time elapses from the application of voltage to the radiation detector, as in the case of the following thirteenth invention, X-rays are emitted in a γ-ray detection period. Thus, it is possible to shorten time required for radiological imaging including an examination for detecting a γ-ray and an examination for detecting an X-ray.

A ninth invention for attaining the above objective is characterized in that the X-rays passing through a test object administered with radiopharmaceutical are detected and γ-rays emitted from the test object due to the radiopharmaceutical in the test object are detected at the position of the test object irradiated with X-rays. According to the ninth invention, since γ-rays are detected at the position of the test object irradiated with X-rays, even when the test object moves during an examination not by movement of a bed, it is possible to improve accuracy of a tomographic image of the test object. The tomographic image is produced using first information obtained by γ-ray detection signals and second information obtained by X-ray detection signals. To be specific, it is possible to accurately combine first tomographic image information and second tomographic image information as described above, thereby improving accuracy of a tomographic image. Improved accuracy of the tomographic image makes it possible to accurately perform diagnosis on a cancer of lymph gland, which is an organelle.

A tenth invention for attaining the above objective is characterized in that γ-rays emitted from a part where radiopharmaceutical concentrates in a test object, X-rays are irradiated onto the test object to detect X-rays passing through the part, and the γ-rays emitted from the part are detected while a bed where the test object is placed exists on a position for detecting the X-rays passing through the part. The tenth invention has the same effect as the ninth invention.

An eleventh invention for attaining the above objective is characterized in that γ-rays are detected by a γ-ray detecting section and X-rays pass through gaps formed on the γ-ray detecting section and are irradiated onto a part of the test object where radiopharmaceutical concentrates. The eleventh invention achieves the same effect as the seventh invention.

A twelfth invention for attaining the above objective is characterized in that γ-rays are detected by a γ-ray detecting section including a plurality of radiation detectors aligned substantially in parallel with the longitudinal direction of a bed, and X-rays are irradiated onto the test object between one end and the other end of the γ-ray detecting section in the above direction. The twelfth invention can achieve the same effect as the first invention.

A thirteenth invention is characterized in that X-rays passing through the test object are detected during a radiological imaging examination period. In the thirteenth invention, since X-rays are detected in the radiological imaging examination period for obtaining a detection signal of a γ-ray, it is possible to shorten time required for radiological imaging including an examination for detecting X-rays and an examination for detecting γ-rays. Besides, the radiological imaging examination period ranges from when detection of γ-rays is started to obtain a γ-ray detection signal required to produce a tomographic image of the test object to when detection of γ-rays is ended to stop the output of the γ-ray detection signal.

A fourteenth invention for attaining the above invention is characterized in that X-rays passing through a test object are detected at some point using some of the plurality of radiation detectors for detecting γ-rays emitted from the test object. According to this characteristic, it is possible to achieve the effect of the thirteenth invention, and it is not necessary to separately provide a radiation detector for detecting γ-rays and a radiation detector for detecting X-rays. The radiation detectors can be commonly used. Thus, it is possible to achieve a compact radiological imaging apparatus. Further, since the radiation detector can be shared for detecting X-rays and γ-rays, it is possible to improve accuracy of a tomographic image produced based on obtained detection signals. Thus, it is possible to improve accuracy of diagnosis on the test object.

A fifteenth invention for attaining the above objective is characterized in that some of a plurality of radiation detectors provided in the radiological imaging apparatus detect X-rays passing through a test object, and when some of the radiation detectors detect the X-rays, the radiation detectors other than some of the radiation detectors detect γ-rays emitted from the test object. In the fifteenth invention, when some of the radiation detectors detect X-rays, radiation detectors other than some of the radiation detectors detect γ-rays, thereby achieving the effect of the thirteenth invention. Further, in the fifteenth invention, when some of the radiation detectors detect X-rays, radiation detectors other than some of the radiation detectors detect γ-rays, so that even when the test object moves during an examination not by movement of a bed, it is possible to improve accuracy of a tomographic image of the test object, the image being produced using first information obtained by a γ-ray detection signal and second information obtained by an X-ray detection signal. Hence, it is possible to improve accuracy of diagnosis on the test object.

It is preferable to detect X-rays in a part of the radiological imaging examination period. Since the X-ray detection period is short, radiation dose applied to the test object by irradiation of X-rays is equal to or less than permissible exposure.

It is preferable to detect the X-rays for obtaining an X-ray detection signal using the radiation detector detecting the γ-rays for obtaining a γ-ray detection signal. Since the X-ray detection signal and the γ-ray detection signal are obtained from each of the radiation detectors, it is possible to improve accuracy of a tomographic image of the examinee.

Other objects, features and advantages of the invention will become apparent from the following description of the embodiments of the invention taken in conjunction with the accompanying drawings.

DETAILED DESCRIPTION OF THE EMBODIMENTS

In the radiological imaging apparatuses described in the above publications, two different examinations are carried out with shifted positions, that is, an examination for detecting X-rays passing through an examinee is carried out, and then, an examination for detecting γ-rays emitted from the examinee is carried out after the examinee is shifted. In such radiological examinations described in the above publications, since the positions of the examinations are inevitably shifted, another problem arises that the correspondence may not be found accurately between pieces of image data obtained by the imaging apparatuses when the examinee moves between the imaging apparatuses or the angle of the examinee changes. This problem was found by the inventor et al. After due study on solutions of the problem, the inventor et al. found the fact that X-rays passing through the examinee administered with radiopharmaceutical are detected and γ-rays emitted by the radiopharmaceutical in the examinee are detected at the position of the examinee irradiated with X-rays, so that image data created by using first information obtained by a γ-ray detection signal can be accurately combined with image data created by using second information obtained by an X-ray detection signal. Further, the inventor et al. also found that the above-described problem can be solved by positioning at least of an X-ray detection part in a region formed between one end and the other end of a γ-ray detecting section in the longitudinal direction of the bed. Specific examples will be discussed below.

(Embodiment 1)

Figure 1:
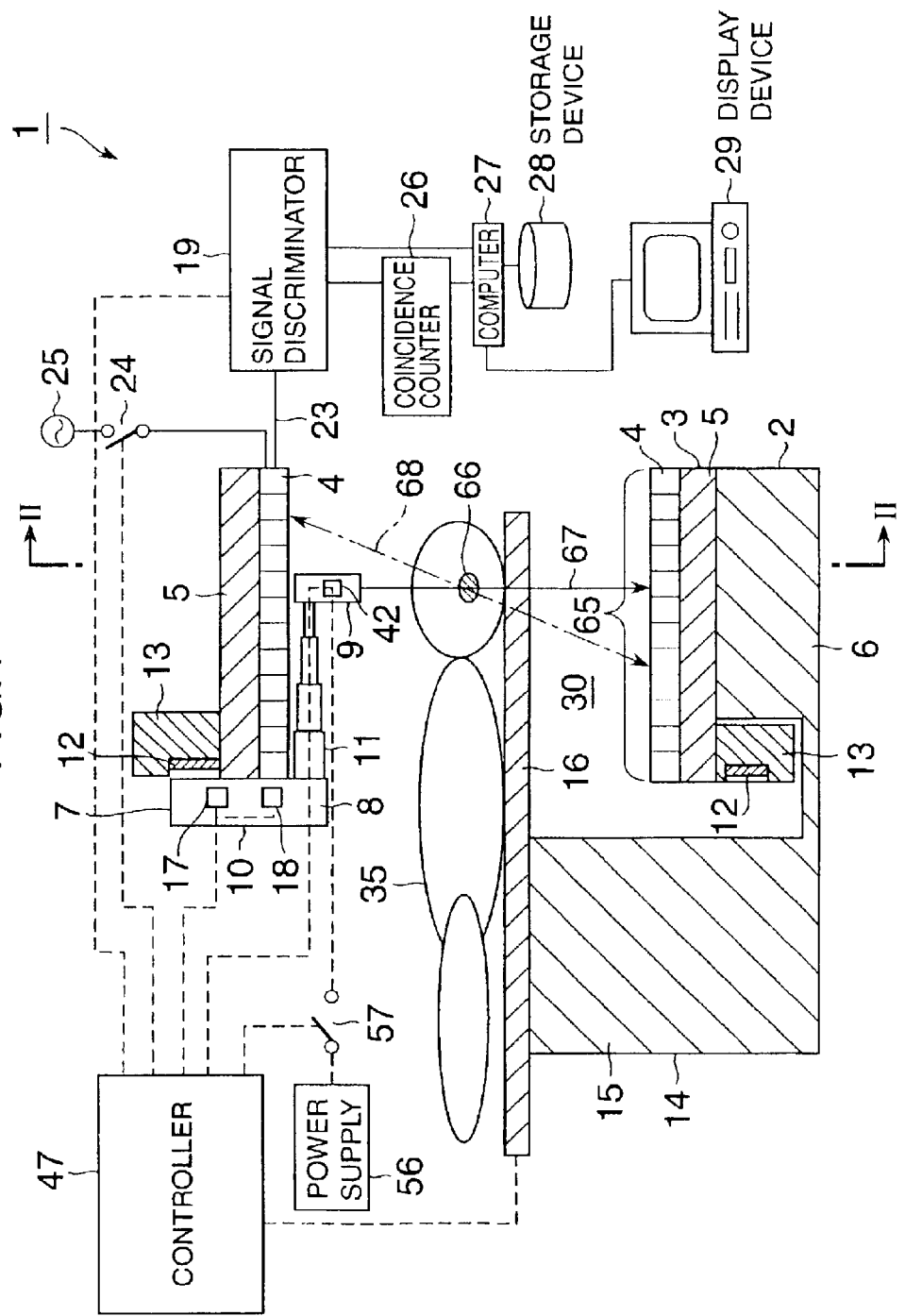
FIG. 1 is a longitudinal sectional view showing a radiological imaging apparatus used for a radiological imaging method according to a preferred embodiment of the present invention.
Figure 2:
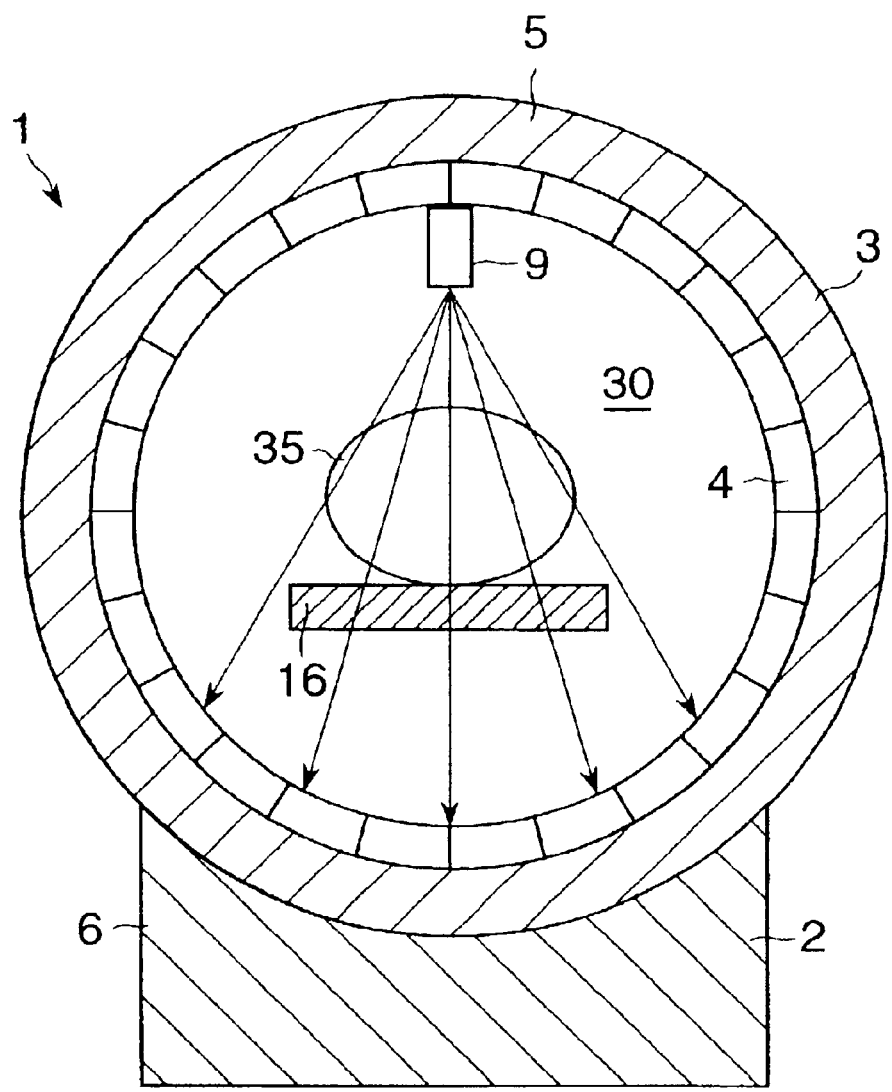
FIG. 2 is a sectional view taken along a line II—II of FIG. 1.

With reference now to FIG. 1 and FIG. 2, a radiological imaging apparatus which is a preferred embodiment of the present invention will be explained below. A radiological imaging apparatus 1 of this embodiment comprises an image pickup apparatus 2, an examinee holding apparatus 14, a signal discriminator 19, a coincidence counter 26, a computer (e.g., a workstation) 27, a storage device 28, a display device 29, and a general controller 47. The examinee holding apparatus 14 includes a supporting member 15 and a bed 16 installed on the top of the supporting member 15 in a manner movable in a longitudinal direction. The image pickup apparatus 2 is installed in a direction perpendicular to the longitudinal direction of the bed 16 and has a radiation detector ring 3 and an X-ray source circumferential transfer device 7. The radiation detector ring 3 includes a ring-shaped holding section 5 and a number of radiation detectors 4 aligned like a ring inside the ring-shaped holding section 5. A through hole section 30 where the bed 16 is inserted is formed inside the radiation detectors 4 of the radiation detector ring 3. A number of radiation detectors 4 (10000 in total) are placed in a plurality of arrays in the axial direction as well as in the circumferential direction of the through hole section 30 in the ring-shaped holding section 5. A number of radiation detectors 4 included in the radiation detector ring 3 constitute a cylindrical radiation detecting section 65. In this embodiment, all the radiation detectors 4 aligned like a ring in the circumferential direction are not moved in the circumferential direction or in the axial direction of the through hole section 30. The radiation detector 4 is a semiconductor radiation detector and has a semiconductor device of a 5-mm cube serving as a detecting section, device consisting of cadmium telluride (CdTe). The detecting section may consist of gallium arsenide (GaAs) or cadmium zinc telluride (CZT). The ring-shaped holding section 5 is placed on the supporting member 6. The supporting members 6 and 15 are connected to each other and are fixed on the floor of an examination room.

The X-ray source circumferential transfer device 7 comprises an X-ray source apparatus 8 and a ring-shaped X-ray source apparatus holding section 13. The X-ray source apparatus holding section 13 is attached on one end of the ring-shaped holding section 5 on the outer surface of the ring-shaped holding section 5. A ring-shaped guide rail 12 is placed on one end of the X-ray source apparatus holding section 13. The guide rail 12 and the X-ray source apparatus holding section 13 surround the through hole section 30. The X-ray source apparatus 8 has an X-ray source 9, an X-ray source drive 10, and an axial transfer arm 11. The X-ray source drive 10 comprises a motor 17 and a power transmission mechanism (not shown) having a reduction gear mechanism in a casing. The power transmission mechanism is connected to the rotational axis of the motor 17. The axial transfer arm 11 is attached to the casing of the X-ray source drive 10 and stretches into the through hole section 30. The X-ray source 9 is attached to the axial transfer arm 11. The axial transfer arm 11 stretches in the axial direction of the through hole section 30 and moves the X-ray source 9 in the axial direction of the through hole section 30. The axial transfer arm 11 stretches in response to driving of the motor 18 placed on the X-ray source drive 10. The X-ray source drive 10 is attached to the guide rail 12 in such a way as not to fall and to be movable along the ring-shaped guide rail 12. The X-ray source drive 10 has a pinion (not shown) to receive a rotational force from the above-described power transmission mechanism. This pinion engages with a rack provided for the guide rail 12.

Figure 3A:
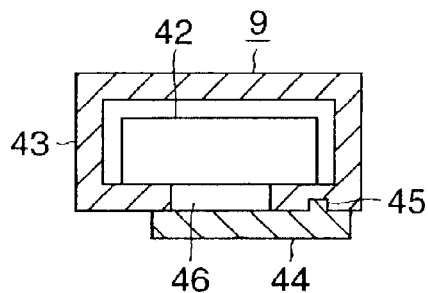
FIG. 3A is a longitudinal sectional view showing an X-ray source of FIG. 1 when a shutter is closed.

As shown in FIG. 3A, the X-ray source 9 has a publicly known X-ray tube 42, a radiation shield 43, and a shutter 44. The X-ray tube 42 is placed in the radiation shield 43 having an opening 46. The shutter 44 constituted by a radiation shielding material is rotatably attached to the radiation shield 43 via an axis 45. The X-ray tube 42 (not shown) comprises a voltage source in an external cylinder to apply voltage among anode, a cathode, a current source for the cathode and between the anode and the cathode. A high-voltage power supply 56 is connected to a current source and a voltage source via a switch 57. Electrons are emitted from a filament when current flows from the current source to the cathode. These electrons are accelerated by a voltage (several hundred kV) applied from the voltage source to between the cathode and the anode and collide with the anode (W, Mo, etc.) which is the target. Collision of electrons with the anode produces X-rays of about 30 to 80 keV. These X-rays 67 are emitted from the opening 46 when the shutter 44 is opened.

Figure 4:
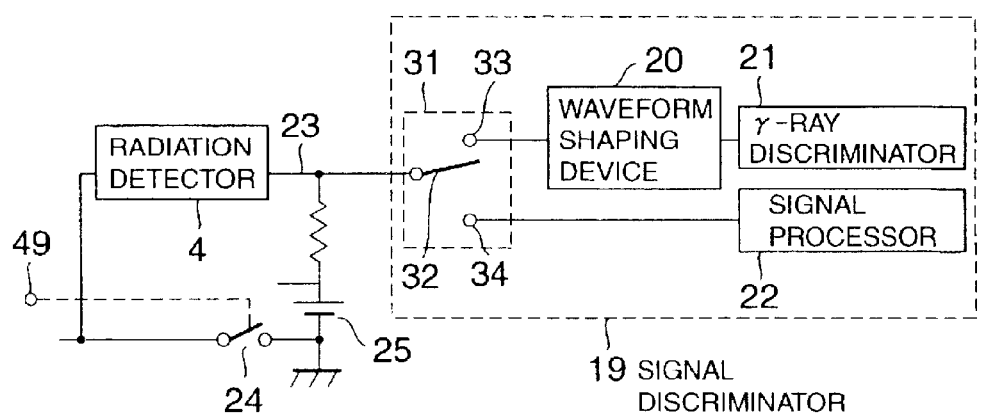
FIG. 4 is a detail structural diagram showing a signal discriminator according to Embodiment 1 shown in FIG. 1.

The radiation detectors 4 are connected to their respective signal discriminators 19 via wiring 23. One signal discriminator 19 is provided for each of the radiation detectors 4. FIG. 4 shows the specific configuration of the signal discriminator 19. The signal discriminator 19 comprises a changeover switch 31, a waveform shaping device 20, a γ-ray discriminator 21, and an X-ray detection signal processor 22 for calculating the intensity of X-rays. The changeover switch 31 serving as a changeover mechanism includes a movable terminal 32 and fixed terminals 33 and 34. The wiring 23 is connected to the movable terminal 32. The waveform shaping device 20 is connected to the fixed terminals 33 and γ-ray discriminator 21. The X-ray detection signal processor 22 is connected to the fixed terminal 34. A plus terminal of a power supply 25 is connected to the wiring 23 via a resistor. The wiring 23 is connected to the radiation detector 4 placed on the radiation imaging apparatus 1. A minus terminal of the power supply 25 is connected to the radiation detector 4 via a power supply switch 24. The γ-ray discriminator 21 is connected to the computer 27 via the coincidence counter 26. One coincidence counter 26 is provided and is connected to the γ-ray discriminator 21. The coincidence counter 26 can also be provided for every several γ-ray discriminators 21. Each of the X-ray detection signal processors 22 is connected to the computer 27. The storage device 28 and the display device 29 are connected to the computer 27. The signal discriminator 19 is a signal processor. This signal processor comprises a first signal processor including the X-ray detection signal processor 22 and a second signal processor including the waveform shaping device 20 and the γ-ray discriminator 21.

Figure 5:
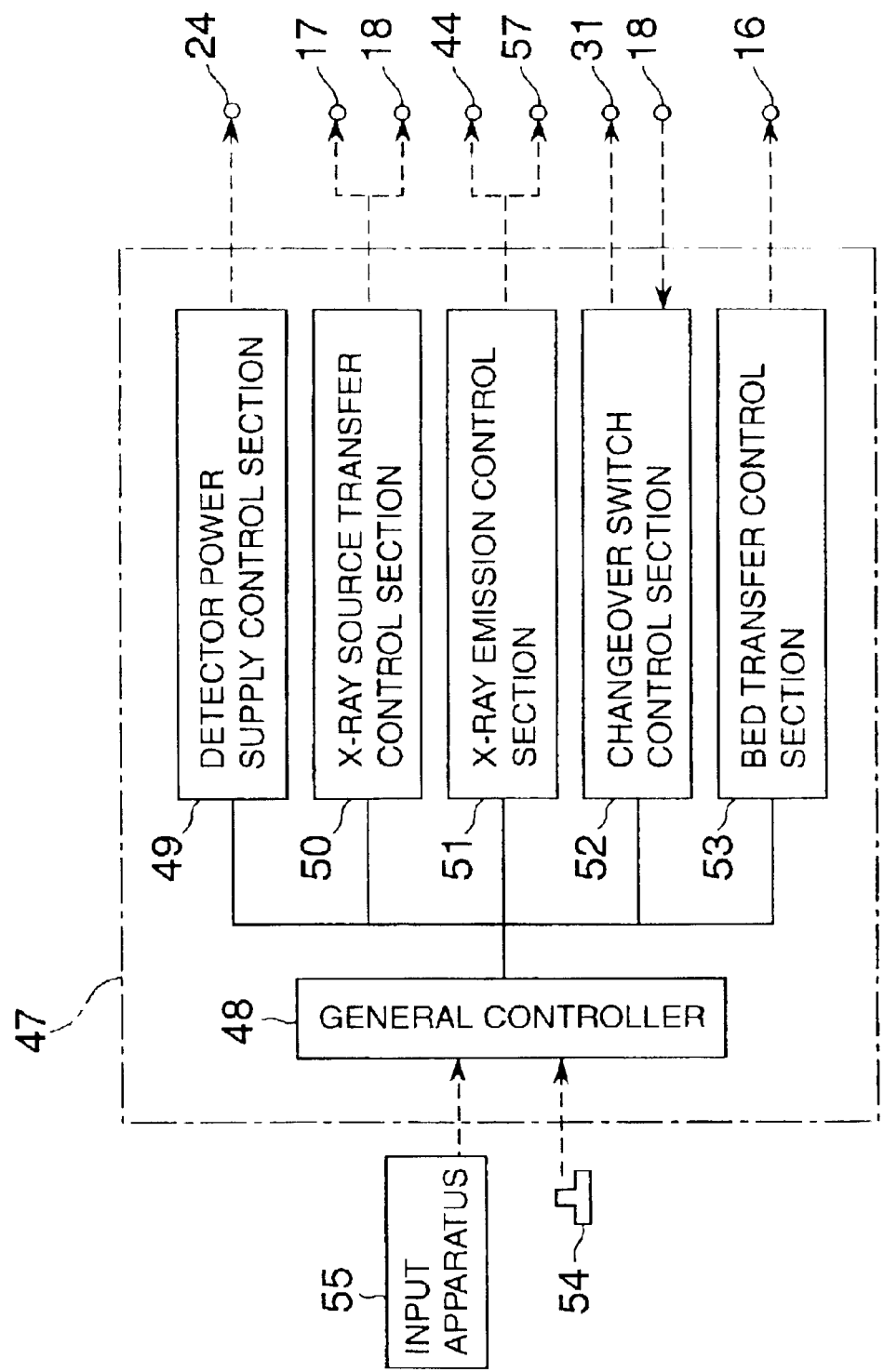
FIG. 5 is a detail structural diagram showing a general controller of FIG. 1.

As shown in FIG. 5, the general controller 47 has a general control section 48, a detector power control section 49, and an X-ray source transfer control section 50, an X-ray emission control section 51, a changeover switch control section 52, and a head transfer control section 53. A button switch 54 and an input apparatus 55 are connected to the general controller 47.

This embodiment shows an example of performing an X-ray computed tomographic examination (action of detecting X-rays 67 which are emitted from the X-ray source 9 and pass through the body of the examinee using the radiation detector) and a PET examination (action of detecting γ-rays 68 emitted due to PET radiopharmaceutical from an affected area 66 existing in the body of an examinee 35, using the radiation detector) using one image pickup apparatus 2.

Before explaining specific examinations in this embodiment, the principles of radiation detection in this embodiment will be explained first. This embodiment is based on the following considerations by the inventor et al. X-ray computed tomographic image data (a tomographic image which is obtained by the X-ray computed tomography and includes images of internal organs and bones of the test object) is created based on the intensity of X-rays detected by a radiation detector by irradiating X-rays emitted from an X-ray source in a specific direction for a predetermined time and repeating (scanning) detection of X-rays passing through the body with the radiation detector. To obtain accurate X-ray computed tomographic image data, it is preferable that no γ-rays emitted due to PET radiopharmaceutical from the body of the test object enter the radiation detector detecting X-rays in an X-ray computed tomographic examination. For this purpose, based on the new knowledge of the inventor et al. that "in one radiation detector, influences of γ-rays are negligible if the time of irradiation with X-rays onto the test object is shortened according to the rate of incidence of γ-rays", this embodiment intends to shorten the time of irradiation onto the examinee with X-rays. To determine the time T of irradiation with X-rays, the rate of incidence of γ-rays into one radiation detector is considered first. Suppose radioactivity in the body based on PET radiopharmaceutical administered to the test object in a PET examination is N (Bq), the rate of generated γ-ray penetration through the body is A, the rate of incidence calculated from a solid angle of one radiation detector is B and the sensitivity of the radiation detector is C. The rate of γ-rays α (rays/sec) detected by one radiation detector is given by Expression (1).

$$\alpha = 2NABC \quad (1)$$

In Expression (1), the coefficient "2" means that a pair (2 rays) of γ-rays are emitted when one positron is annihilated. A probability W that γ-rays will be detected by one detecting device for irradiation time T is given by Expression (2).

$$W = 1 - \exp(-T\alpha) \quad (2)$$

By determining the irradiation time T in such a way that the value of W in Expression (2) is reduced, influences of γ-rays entering one radiation detector becomes as small as negligible during an X-ray computed tomographic examination.

An example of X-ray irradiation time T will be explained below. A specific X-ray irradiation time T was calculated based on Expressions (1) and (2). The intensity of radiation in the body caused by radiopharmaceutical to be administered to the examinee in a PET examination is on the order of a maximum of 370 MBq (N=370 MBq) and the penetration rate A of γ-rays through the body is on the order of 0.6 (A=0.6) if the body of the test object is supposed to be water having a radius of 15 cm. For example, if radiation detectors of 5 mm per side are arranged in a ring form of 50 cm radius, the rate of incidence B calculated from the solid angle of one radiation detector is $8 \times 10^{-6}$ (B=$8 \times 10^{-6}$). Furthermore, the detection sensitivity C of the radiation detector is on the order of a maximum of 0.6 (C=0.6) when a semiconductor radiation detector is used. From these values, the γ-ray detection rate α of one radiation detector is on the order of 2000 (rays/sec). Suppose X-ray irradiation time T is 1.5 μsec, for example. The probability W that one radiation detector will detect γ-rays during X-ray detection is 0.003. For this reason, γ-rays are almost negligible. In the case where radioactivity doses into the body are 360 MBq or less, if X-ray irradiation time is 1.5 μsec or less, W<0.003, that is, the γ-ray detection probability becomes 0.3% or less, which is negligible.

Before conducting radiological imaging, the examinee 35 is administered with PET radiopharmaceutical beforehand by means of injection so that radioactivity doses into the body are 370 MBq or less. The examinee 35 is a test object. The PET radiopharmaceutical is selected according to the examination purpose (localizing cancer or inspecting the arterial flows of the heart, etc.). The PET radiopharmaceutical administered to the examinee 35 concentrates on the affected area (e.g., an area of cancer) 66 of the examinee 35. The examinee 35 administered with the PET radiopharmaceutical is laid down on the bed 16 on the examinee holding apparatus 14. The bed 16 is withdrawn from the image pickup apparatus 2 at that time.

Figure 6:
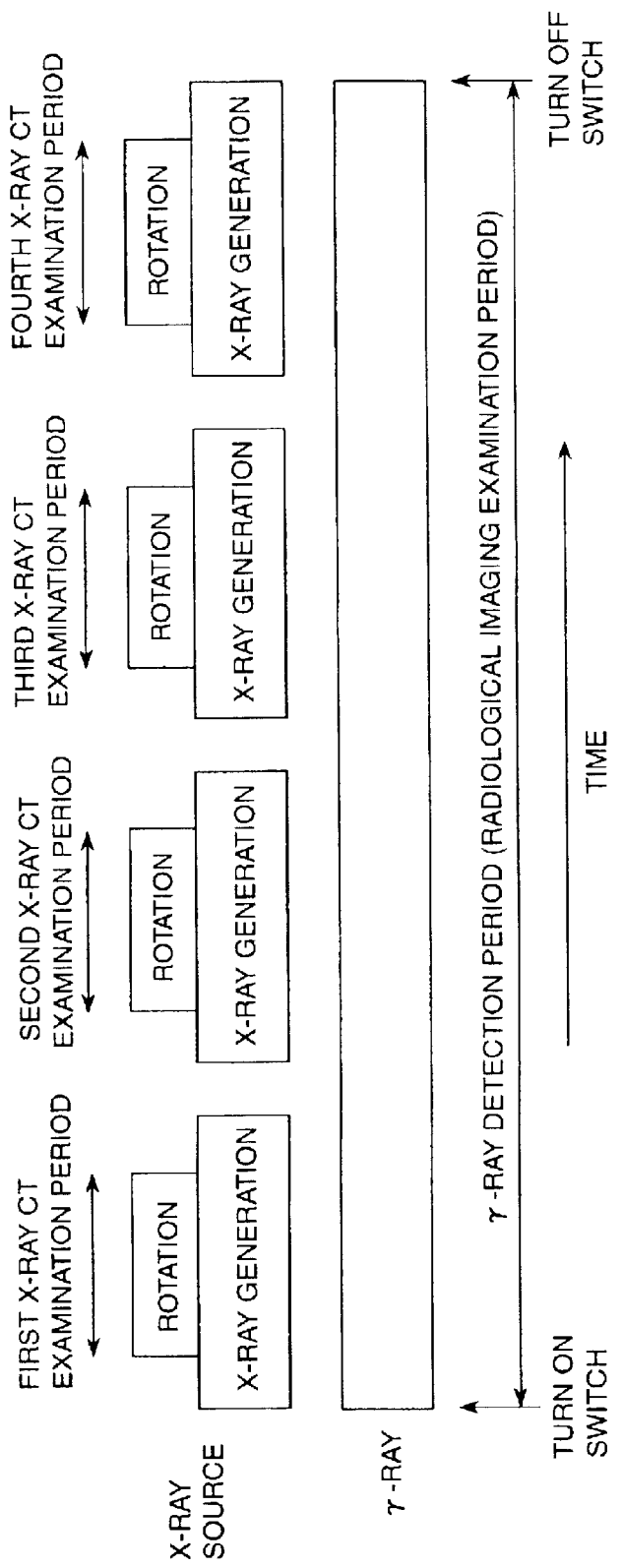
FIG. 6 is an explanatory drawing showing a control schedule applied to the radiological imaging method of this embodiment.

Before starting radiological imaging, an operator (e.g., a radiologic technologist) of the radiological imaging apparatus inputs an examination range and the number of times of X-ray computed tomographic examinations on the examinee 35 by using the input apparatus 55. These pieces of information are inputted to a controller storage device (not shown) of the general controller 47 and are inputted to the general controller 48. The through hole section 30 on the examination range is shorter than, for example, the radiation detector ring 3 in the axial direction. The general controller 48 computes time required for the PET examination based on the pieces of information and sets a period of the PET examination that is equivalent to a period of γ-ray detection period, starting time of X-ray detection (starting time of X-ray computed tomographic examination) in the period of the PET examination, and a period of X-ray computed tomographic examination which is equivalent to an X-ray detection period. This operation makes it possible to produce an example of a control schedule including the starting time of X-ray computed tomographic examination as shown in FIG. 6. The information of the created control schedule is stored in a controller storage device. Since the control schedule is displayed on a display device (not shown), the operator can look at the schedule. The control schedule has four X-ray computed tomographic examinations performed during the PET examination.

When the radiological imaging is started, the operator presses a button switch 54 to input an examination start signal to the general controller 48. When the examination start signal is inputted, the general controller 48 outputs a bed transfer start signal and the information about the examination range of the examinee 35 to the bed transfer control section 53. The information has been stored in the controller storage device. The bed transfer control section 53 rotates a motor (not shown) for transferring the bed according to the bed transfer start signal and the information about examination range, the motor being provided on the supporting member 55 to transfer the bed 16, and the bed transfer control section 53 transfers the bed 16 such that the examination range of the examinee 35 enters the through hole section 30.

In this state, an X-ray computed tomographic examination and a PET examination are carried out using the present embodiment. These examinations are conducted using the image pickup apparatus 2. The content of these examinations will be specifically discussed below.

The general controller 47 controls the power supply of the radiation detector 4, the transfer of the X-ray source, the transfer of the bed, the switching of the changeover switch 31, and X-ray emission from the X-ray source 9. The following will discuss the functions of the general controller 47 in order. First, when an examination start signal is inputted, the general control section 48 outputs a power supply ON signal to the detector power supply control section 49. When the power supply ON signal is inputted, the detector power supply control section 49 closes the power supply switch 24. Voltage of the power supply 25 is applied to the radiation detectors 4, so that the radiation detectors 4 can detect γ-rays and X-rays. The pair of γ-rays 68 which are caused by the PET radiopharmaceutical concentrating on the affected area 66 of the examinee 35 and are emitted from the body with energy of 511 keV is detected by the radiation detectors 4 of the radiation detector 65 in response to the closing of the power supply switch 24. The period of the γ-ray detection (see FIG. 6) is started by closing the power supply switch 24. The period of the γ-ray detection is the radiological imaging examination period. A number of γ-ray pairs are emitted in all directions from the affected area 66. The general control section 48 outputs an X-ray tube starting signal to the X-ray emission control section 51 at a predetermined time prior to the starting time of the X-ray computed tomographic examination in the first X-ray computed tomographic examination of the control schedule. The X-ray emission control section 51 outputs a first switch closing signal in response to the signal and closes the switch 57. Voltage is applied to the voltage source of the X-ray tube 42 from the high-voltage power supply 56, and current flows to a current source. After a while, as described above, X-rays are generated on the X-ray tube 42. At this moment, the shutter 44 is closed and the X-rays are not emitted to the outside of the X-ray source 9.

From the examinee 35 who is inserted into the through hole section 30 and is laid down on the bed 16, the γ-rays 68 are emitted thus and are detected by the radiation detectors 4 of the radiation detecting section 65. The radiation detectors 4 which detect the γ-rays 68 output γ-ray detection signals serving as detection signals. The γ-ray detection signals are inputted to their respective signal discriminators 19 via the corresponding wiring 23 and are processed as will be discussed later. The X-ray source 9 is stored in the X-ray source drive 10 by causing the axial transfer arm 11 to contract in such a way as not to interfere with detection of the γ-rays 68 using the radiation detectors 4.

Figure 3B:
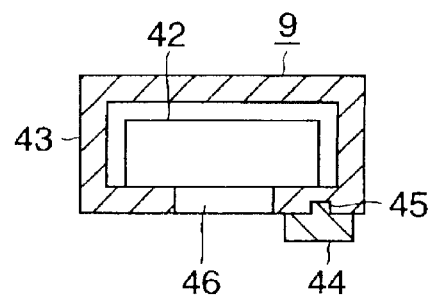
FIG. 3B is a longitudinal sectional view showing the X-ray source of FIG. 1 when the shutter is opened.

Before the X-ray computed tomographic examination start signal is outputted, the general control section 48 outputs a first X-ray source transfer signal to the X-ray source transfer control section 50. In response to the signal, the X-ray source transfer control section 50 outputs a second switch closing signal. Thus, a second switch (not shown) connected to the motor 18 and the power supply is closed, and the X-ray source 9 moves in the axial direction of the through hole section 30 by the driving of the motor 18. When the X-ray source 9 moves to a predetermined position within the examination range, the X-ray source transfer control section 50 outputs a second switch opening signal to open the second switch. Thus, the movement of the X-ray source 9 in the axial direction of the through hole section 30 is stopped. Thereafter, the general control section 48 outputs the X-ray computed tomographic examination start signal to the X-ray source transfer control section 50, the X-ray emission control section 51, and the changeover switch control section 52. The X-ray emission control section 51 outputs a shutter opening signal to close the second switch (not shown) connecting the motor (not shown) for the shutter and the power supply. The motor for the shutter is driven to open the shutter 44 (see FIG. 3B). The X-rays 67 generated in the X-ray tube 42 are emitted through the opening 46 and are radiated in the form of fan beams onto the examinee 35 on the bed 16. When the X-ray computed tomographic examination start signal is inputted, the X-ray source transfer control section 50 outputs an X-ray source rotation start signal to close a first switch (not shown) connecting the motor 17 and the power supply. The pinion is rotated by the rotation of the motor 17. Therefore, the X-ray source apparatus 8 moves along the guide rail 12 and the X-ray source 9 moves around the examinee 35 at a set speed. In this way, an X-ray computed tomographic examination is started.

The X-ray emission control section 51 controls the time for emitting the X-rays 67 from the X-ray source 9. Namely, in the X-ray computed tomographic examination, the X-ray emission control section 51 outputs the shutter opening signal and the shutter closing signal alternately in a first set time and a second set time to control the opening/closing of the shutter. Thus, the emission and stopping of the X-rays 67 from the X-ray source 9 is controlled. This control causes the shutter 44 to open during the first set time and to close during the second set time. Consequently, X-rays are emitted in the form of pulse from the X-ray source 9. Irradiation time T serving as the first set time is set at, for example, 1 µsec such that the detection probability of the γ-rays 68 becomes negligible on the radiation detectors 4. The second set time is time T0 during which the X-ray source 9 moves between one radiation detector 4 and another radiation detector adjacent thereto in the circumferential direction and is determined by the moving speed of the X-ray source 9 in the circumferential direction of the guide rails 12. The first and second set times are stored in the controller storage device.

These X-rays 67 which are radiated onto the examinee 35 and pass through the examinee 35 are detected by a plurality of radiation detectors 4 placed in the circumferential direction centered on the radiation detector 4 which is located at 180° from the X-ray source 9 with the axial center of the through hole section 30 as the base point. These radiation detectors 4 output X-ray detection signals serving as detection signals of the X-rays 67. These X-ray detection signals are input to their respective signal discriminators 19 through their respective wirings 23. In the radiation detecting section 65, the radiation detectors 4 detecting the above-described X-rays are called "first radiation detectors 4" for the sake of convenience. Further, in the radiation detecting section 65, the radiation detectors 4 detecting γ-rays are called "second radiation detectors 4" for the sake of convenience. Since the axial transfer arm 11 is stretched by the control of the X-ray source transfer control section 50 during an X-ray computed tomographic examination, the X-ray source 9 is moved in the axial direction of the through hole section 30 within the examination range. When the X-rays 67 emitted from the X-ray source 9 pass through an affected area 66 of the examinee 35, the first radiation detector 4 detects the X-rays 67 passing through the affected area 66.

The following will discuss the changeover control of the changeover switch 31. In the signal discriminators 19, γ-ray detection signals outputted from the second radiation detectors 4 are transmitted to the γ-ray discriminator 21, and the X-ray detection signals outputted from the first radiation detectors 4 are transmitted to the X-ray detection signal processor 22. Such transmission of the detection signals is switched by the changeover control performed by the changeover switch 31 or the signal discriminator 31. The changeover operation of connecting the movable terminal 32 of the changeover switch 31 to the fixed terminal 33 or the fixed terminal 34 is performed based on a first changeover signal and a second changeover signal which are outputted from the changeover switch control section 52 after the X-ray computed tomographic examination start signal is inputted. The first changeover signal connects the movable terminal 32 to the fixed terminal 33 and the second changeover signal connects the movable terminal 32 to the fixed terminal 34. The changeover switch control section 52, which is fed the X-ray computed tomographic examination start signal, selects the first radiation detector 4, outputs the second changeover signal to the changeover switch 31 where the selected first radiation detector 4 is connected, and connects the movable terminal 32 to the fixed terminal 34.

The first radiation detector 4 is selected in the changeover control section 52 as discussed below. The changeover switch control section 52 inputs a detection signal of an encoder 58 (see FIG. 5) connected to the motor 17 and finds the position of the X-ray source drive 10, that is, the X-ray source 9 in the circumferential direction, and selects the radiation detector 4 placed 180° opposite to the position of this X-ray source 9 using the stored position data of the radiation detectors 4. X-rays 67 emitted from the X-ray source 9 has a certain breadth in the circumferential direction of the guide rails 12, and therefore there is a plurality of radiation detectors 4 that detect X-rays passing through the body of the examinee 35 in the circumferential direction in addition to the selected radiation detector 4. The changeover switch control section 52 also selects the plurality of radiation detectors 4. These radiation detectors 4 are the first radiation detectors. As the X-ray source 9 moves in the circumferential direction, the first radiation detectors 4 also change. It seems that the first radiation detectors 4 also move in the circumferential direction together with the circumferential movement of the X-ray source 9. When the changeover switch control section 52 selects another radiation detector 4 in response to the detection signal of the encoder 58 as the X-ray source 9 moves in the circumferential direction, the second changeover signal is inputted to the changeover switch 31 connected to the new radiation detector 4, and the movable terminal 32 is connected to the fixed terminal 34. Moreover, the changeover switch control section 52 outputs the first changeover signal to the changeover switch 31 connected to the new radiation detector 4 which is no more the first radiation detector 4, and connects the movable terminal 32 to the fixed terminal 33. The above-described changeover control of the changeover switch is carried out in order during the X-ray computed tomographic examination.

When the first X-ray examination of FIG. 6 is completed, the general control section 48 outputs X-ray computed tomographic examination end signals respectively to the X-ray source transfer control section 50, the X-ray emission control section 51, and the changeover switch control section 52. The following will discuss the functions of the three control sections which are fed the x-ray computed tomographic examination end signals. First, the X-ray source transfer control section 50 outputs an X-ray source rotation stop signal, opens the first switch to stop the rotation of the motor 17, and stops the rotation of the X-ray source 9. The X-ray source transfer control section 50 outputs a second switch closing signal to close the second switch, reverses the motor 18 to cause the axial transfer arm 11 to contract, and stores the X-ray source 9 in the X-ray source drive 10. The X-ray emission control section 51 outputs a shutter closing signal to close the shutter 44. The closing of the shutter 44 stops irradiation of X-rays 67 onto the examinee 35. The shutter 44 is closed immediately after the X-ray computed tomographic examination end signal is inputted. The X-ray emission control section 51 further outputs the first switch opening signal to open the switch 57 and stops application of voltage to the X-ray tube 42 from the high-voltage power supply 56. The changeover switch control section 52 outputs the first changeover signals to all of the changeover switches 31 where the movable terminals 32 are connected to the fixed terminals 34 and connects the movable terminals 34 of the changeover switches 31 to the fixed terminals 33.

When the set time elapsed after the first X-ray computed tomographic examination is completed, to carry out the second X-ray computed tomographic examination, the control sections of the general controller 47 perform the above-described control. In the third and fourth X-ray computed tomographic examinations as well, the general controller 47 performs the same control. When the fourth X-ray computed tomographic examination is completed and the remaining PET examinations are completed, the general control section 48 outputs a power supply OFF signal to the detector power supply control section 49 to end the radiological imaging. The detector power supply control section 49 opens the power supply switch 24 in response to the signal. Thus, application of voltage to the radiation detectors 4 is stopped. The above-described control completes the radiological imaging.

The information of the above-described control schedule includes time information for outputting the bed transfer start signal, the power supply ON signal, the X-ray tube starting signal, the first X-ray source transfer signal, the X-ray computed tomographic examination start signal, the X-ray computed examination end signal, and the power supply OFF signal after the examination start signal is inputted. Besides, the number of pieces of the time information for outputting the X-ray tube starting signal, the first X-ray source transfer signal, the X-ray computed tomographic examination start signal, and the X-ray computed examination end signal is equivalent to the number of times of the X-ray computed tomographic examinations performed in the radiological imaging examination period. In the times specified by the time information included in the control schedule information, the general control section 48 outputs their respective control signals to the corresponding control sections in the general controller 47.

During the radiological imaging examination period, the γ-rays 68 emitted from the affected area 66 of the examinee 35 can be detected by the second radiation detector 4 in the case where the X-ray computed tomographic examination is carried out as well as in the case where the X-ray computed tomographic examination is not carried out. Hence, according to this embodiment, the PET examination can be carried out even when the X-ray computed tomographic examination is performed. In other words, the X-ray computed tomographic examination can be performed even during the period of the PET examination.

The individual radiation detectors 4 of the radiation detecting section 65 sometimes serve as the first radiation detector 4 and sometimes serve as the second radiation detector 4 in accordance with the position from the X-ray source 9. For this reason, the individual radiation detectors 4 separately output both of the X-ray detection signal and the γ-ray detection signal. The first radiation detector 4 detects the X-rays 67 passing through the examinee 35 for 1 μsec, which is equivalent to the first set time. As described above, the probability that the first radiation detector 4 detects the γ-rays 68 emitted from the affected area 66 of the examinee 35 is as small as negligible. Many γ-rays 68 generated by PET radiopharmaceutical on the affected area 66 of the examinee 35 are not emitted in a specific direction but are emitted in all directions. As described above, the γ-rays 68 are emitted in pairs substantially in opposite directions and are detected by any one of the second radiation detectors 4 of the radiation detecting section 65.

The following will discuss signal processing of the signal discriminator 19 when X-ray detection signals and γ-ray detection signals outputted from the radiation detectors 4 are inputted. The X-ray image detection signals outputted from the first radiation detectors 4 are inputted to the X-ray detection signal processor 22 via the fixed terminal 34 of the changeover switch 31 as described above. The X-ray detection signal processor 22 integrates the X-ray detection signals for each set period using an integrator and outputs the integrated value of the X-ray detection signals for each set period, that is, information on the intensity of the X-rays. The X-ray detection signal processor 22 outputs position information on detection of X-rays that includes positions of the radiation detectors 4 connected to the X-ray detection signal processor 22 together with the information on the intensity of the X-rays.

Figure 7:
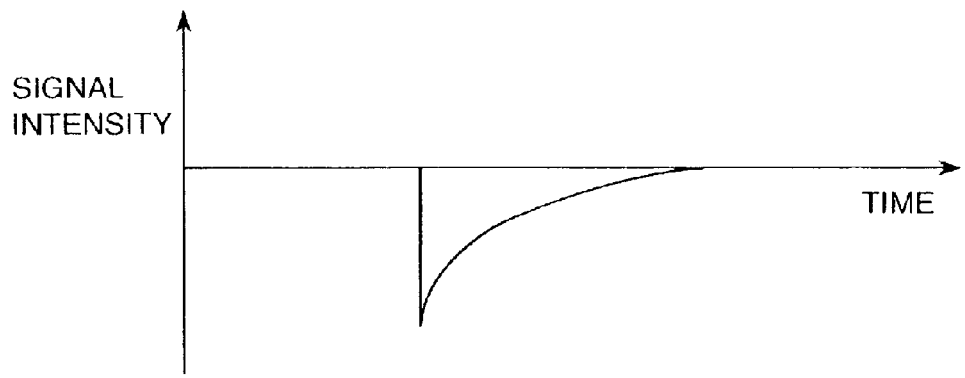
FIG. 7 is an explanatory drawing showing a waveform of a γ-ray detection signal inputted to a waveform shaping device of FIG. 4.
Figure 8:
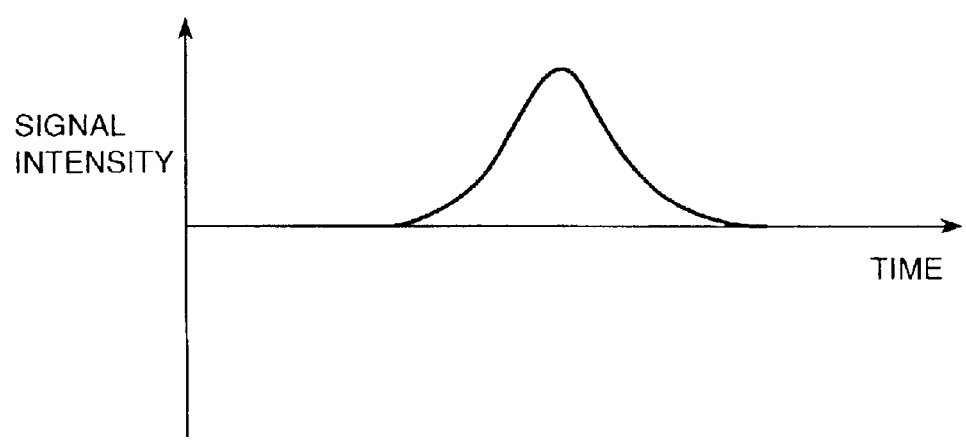
FIG. 8 is an explanatory drawing showing a waveform of a γ-ray detection signal outputted from the waveform shaping device of FIG. 4.

The γ-ray detection signals outputted from the second radiation detectors 4 are inputted to the waveform shaping device 20 via the fixed terminal 33 of the changeover switch 31. The γ-ray detection signals inputted to the waveform shaping device 20 falls abruptly in the beginning and then comes closer to 0 at an exponential rate as shown in FIG. 7. To smoothly process the γ-ray detection signal in the γ-ray discriminator 21, the waveform shaping device 20 converts the γ-ray detection signal having the waveform shown in FIG. 7 to, for example, a waveform of a Gaussian distribution on the time axis as shown in FIG. 8 and outputs the signal. Incidentally, all the energy of the γ-rays of 511 keV is not always changed to charges in the semiconductor device of the radiation detector 4. Thus, the γ-ray discriminator 21 uses energy of 450 keV, which is lower than 511 keV, as a first energy set value and generates a pulse signal having predetermined energy when a γ-ray detection signal having energy equal to or greater than this energy set value is inputted. That is, the γ-ray discriminator 21 is an apparatus that generates a pulse signal having the above-described energy when a γ-ray detection signal having energy equal to or greater than the first energy set value is inputted. The γ-ray discriminator 21 is a γ-ray detection signal processor and adds time information and position information, which is indicative of positions of the radiation detectors 4 connected to the γ-ray discriminator 21, to a pulse signal to be outputted. The time information is one of time for inputting a γ-ray detection signal to the γ-ray discriminator 21 and time for outputting a pulse signal from the γ-ray discriminator 21.

As described above, to process a γ-ray detection signal having energy equal to or greater than the first energy set value in the γ-ray discriminator 21, a first filter is provided inside the γ-ray discriminator 21 (or on the previous stage of the γ-ray discriminator 21) to allow passage of a γ-ray detection signal having energy equal to or greater than the first energy set value. The γ-ray discriminator 21 generates a pulse signal for the γ-ray detection signal that has passed through the first filter.

The coincidence counter 26 is fed a pulse signal outputted from the γ-ray discriminator 21 of the signal discriminator 19. The coincidence counter 26 carries out coincidence counting using pulse signals corresponding to γ-ray detection signals outputted from two of the second radiation detectors (a pair of second radiation detectors which have a difference in position of almost 180° (strictly speaking 180°±0.6°) and are centered on the axial center of the through hole section 30)) for detecting the γ-rays 68 of the γ-ray pair, and the coincidence counter 26 calculates a count rate (γ-ray count rate information) for the γ-ray detection signal. The coincidence counter 26 judges whether the pulse signals correspond to detection signals of γ-rays in the γ-ray pair based on the time information added to the pulse signals. Namely, when two pieces of time information have a difference equal to or less than set time (e.g., 10 nsec), it is judged that the pulse signal corresponds to the pair of γ-rays 68 generated by disappearance of one proton. Additionally, the coincidence counter 26 datarizes the position information added to the pulse signals as position information of the corresponding pair of the second radiation detectors 4, that is, position information of the γ-ray detection points.

The γ-ray discriminator 21 and the coincidence counter 26 constitute the first signal processor which is used for reconstruction of a tomographic image and generates first information including γ-ray count rate information and position information of γ-ray detection points for γ-ray pairs. The X-ray detection signal processor 22 is the second signal processor which is used for reconstruction of a tomographic image and generates second information including information on intensity of X-rays and position information on detection of X-rays. To be specific, the position information of the γ-ray detection points is position information of the radiation detector 4 for detecting γ-rays. To be specific, the position information of the X-ray detection is position information of the radiation detector 4 which detected X-rays. The coincidence counter 26 is fed output signals from the γ-ray discriminators 21 serving as γ-ray detection signal processors and outputs first information required for creation of first tomographic image information (to be specific, PET image data).

Figure 9:
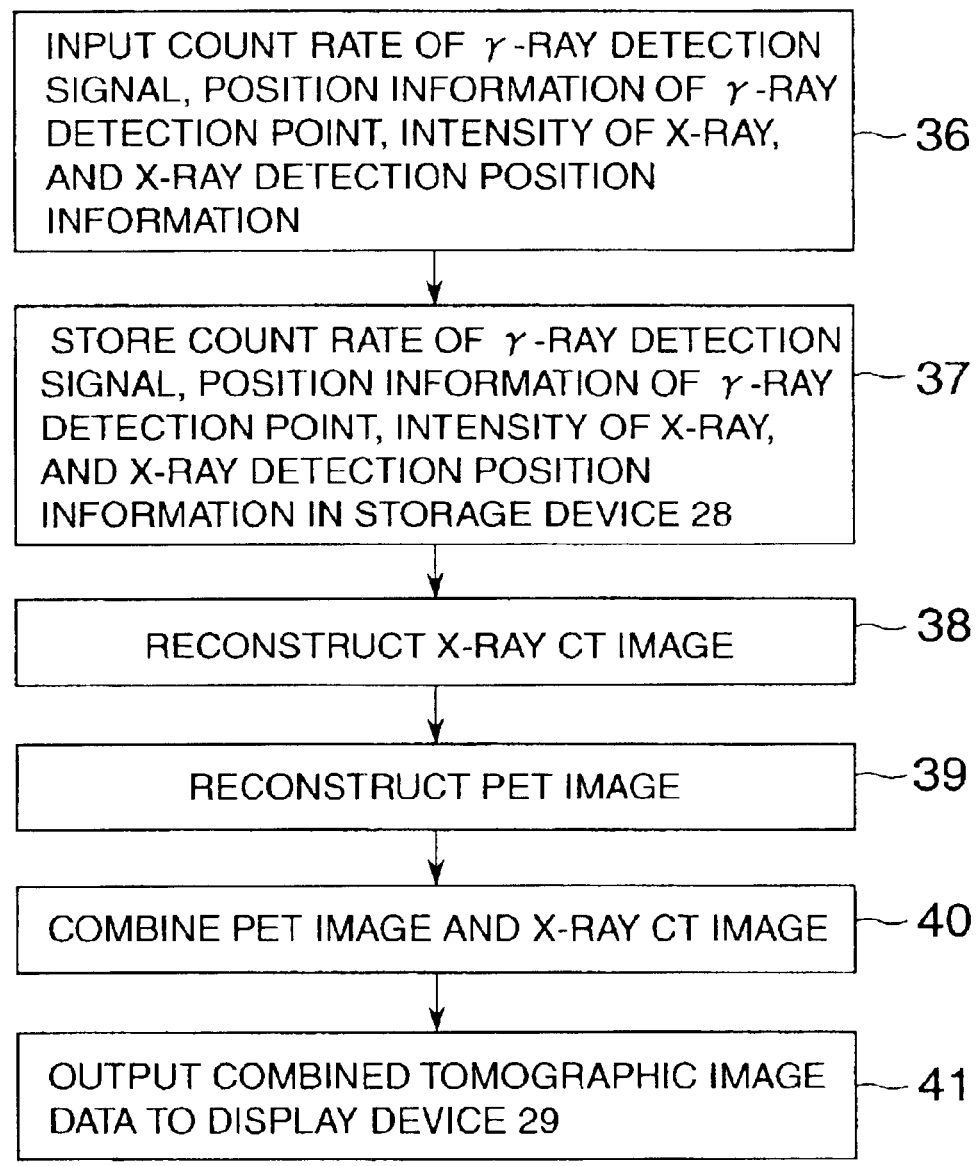
FIG. 9 is a flowchart showing a procedure performed by a computer.

The computer 27 executes processing based on the procedure in steps 36 to 41 shown in FIG. 9. The computer 27 carrying out such processing is an apparatus for creating tomographic image data that creates first tomographic image information using first information (to be specific, γ-ray count rate information and position information on γ-ray detection points), creates second tomographic image information (to be specific, X-ray computed tomographic image data) using second information (to be specific, information on intensity of X-rays and information on X-ray detection positions), and creates third tomographic image information (to be specific, combined tomographic image data) using the first tomographic image information and the second tomographic image information. The count rate of the γ-ray detection signal counted by the coincidence counter 26, position information of the γ-ray detection point outputted from the coincidence counter 26, information on intensity of X-rays outputted from the X-ray detection signal processor 22, and position information of X-ray detection added to the intensity of the X-ray are inputted (step 36). The inputted count rate information of the γ-ray detection signal, position information of the γ-ray detection point, information on intensity of X-rays, and position information of X-ray detection are stored in the storage device 28 (step 37).

A tomography image on a cross section of the examinee 35 (hereinafter, a cross section refers to a cross section in which the examinee stands up) is reconstructed (step 38). The reconstructed tomographic image is referred to as an X-ray computed tomographic image. The specific procedure for reconstructing the tomographic image will be discussed below. First, an attenuation rate of X-rays in the body of the examinee 35 is calculated for each voxel using information on intensity of X-rays. In the present embodiment, an attenuation rate of X-rays for each voxel is calculated using information on intensity of X-rays. The information is obtained from X-ray detection signals detected by four X-ray computed tomographic examinations. The attenuation rate is stored in the storage device 28. To reconstruct the X-ray computed tomographic image, a linear attenuation coefficient in the body of the examinee 35 between the position of the X-ray source 9 and the position (obtained from position information on X-ray detection) of the radiation detector 4 which has detected X-rays is calculated by using an attenuation rate of an X-ray detection signal read from the storage device 28. The positions of the X-ray source 9 during movement that is detected by the encoder 58 is added to information on intensity of X-rays by the X-ray detection signal processors 22 and is conveyed to the computer 27. Using the linear attenuation coefficient, a CT value at each voxel is calculated based on a value of the linear attenuation coefficient at each voxel, the coefficient being obtained according to the filtered back projection method. Data of the X-ray computed tomographic image is obtained by the CT values and is stored in the storage device 28. In the step 38, an X-ray computed tomographic image showing a cross section of an affected area with concentrated PET radiopharmaceutical can be also reconstructed.

A tomographic image including an affected area (e.g., a cancer) of the examinee 35 in cross section is reconstructed using a count rate of a γ-ray detection signal at the corresponding position (step 39). A tomographic image reconstructed using a count rate of a γ-ray detection signal will be referred to as a PET image. The processing will be discussed in detail. Using the count rate of the γ-ray detection signal read from the storage device 28, the number of γ-ray pairs in the body (the number of γ-ray pairs generated by annihilation of a plurality of positrons) between the semiconductor devices of a pair of the second radiation detectors 4 (specified by position information of the γ-ray detection point) is calculated. The second radiation detectors 4 have detected γ-rays generated by annihilation of protons. Using the number of generated γ-ray pairs, density of generated γ-rays at each voxel is calculated according to filtered back projection method. It is possible to obtain data of a PET image based on the density of generated γ-ray pairs. The data of the PET image is stored in the storage device 28.

The data of the PET image and the data of the X-ray computed tomographic image are combined to obtain data of a combined tomographic image including both pieces of data, and the data is stored in the storage device 28 (step 40). PET image data on an affected area and X-ray computed tomographic image data thereon are combined with each other to obtain combined tomographic image data on the affected area of the examinee 35 in cross section. Combination of PET image data and X-ray computed tomographic image data can be performed easily and accurately by aligning the central axis of the through hole section 30 in both image data pieces. That is, the PET image data and X-ray computed tomographic image data are created based on the detection signals outputted from the common radiation detector 4, and therefore alignment can be performed accurately as described above. The combined tomographic data is called from the storage device 28 and outputted to the display device 29 (step 41) and displayed on the display device 29. The combined tomographic image displayed on the display device 29 includes an X-ray computed tomographic image, and therefore it is possible to easily check the position in the body of the examinee 35 of the affected area in the PET image. That is, since the X-ray computed tomographic image includes images of internal organs and bones, doctors can identify the position of the affected area (e.g., the affected area of cancer) from the positions of the internal organs or bones.

Besides, an X-ray computed tomographic image requires a plurality of scan data pieces, and therefore the required amount of data can be calculated from the radiation detector 4 by moving the X-ray source 9 along the guide rail 12 using the X-ray source drive 10. Through this circumferential scanning of the X-ray source 9, this embodiment obtains two-dimensional sectional data about an X-ray detection signal on one cross section of the examinee 35. The two-dimensional sectional data about an X-ray image detection signal on another cross section can be obtained by stretching the axial transfer arm 11 and moving the X-ray source 9 in the axial direction of the through hole section 30. By accumulating these two-dimensional sectional data pieces, it is possible to obtain three-dimensional sectional data. Using these three-dimensional sectional data pieces, it is possible to obtain three-dimensional X-ray computed tomographic image data. Furthermore, by continuously stretching the axial transfer arm 11 in the axial direction of the through hole section 30 as the X-ray source 9 rotates, it is also possible to perform a helical scan of X-rays. Two-dimensional sectional data on the X-ray detection signal on another cross section can also be obtained by transferring the bed 16 in the axial direction of the through hole section 30 instead of stretching the axial transfer arm 11.

In this embodiment, since the radiation detecting section 65 is constituted by a plurality of radiation detectors 4 for outputting both of an X-ray detection signal and a γ-ray detection signal, the radiation detecting section 65 serves as a γ-ray detecting section as well as an X-ray detecting section. In this embodiment, the X-ray detecting section is placed in a region formed between one end and the other end of the γ-ray detecting section in the longitudinal direction of the bed 16. Further, the radiation detecting section 65 serves as an X-ray detecting section for detecting the X-rays 67 and outputting detection signals of the X-rays 67 which are irradiated from the X-ray source 9 and pass through the examinee 35. The radiation detecting section 65 also serves as a γ-ray detecting section for detecting the γ-rays 68 and outputting detection signals of the γ-rays 68. The γ-rays 68 are emitted due to PET radiopharmaceutical from a part (affected area 66) having X-rays 67 transmitted in the examinee 35 at a position of the examinee 35 where the X-rays 67 are irradiated. The image pickup apparatus 2 which has the γ-ray detecting section and the X-ray detecting section is a radiation detecting device.

This embodiment can produce the following effects:

(1) In this embodiment, in a part of the radiological imaging examination period for detecting γ-rays emitted from the examinee 35 used as an examinee, X-rays passing though the examinee 35 are detected while γ-rays are detected, and therefore it is possible to carry out an X-ray computed tomographic examination while conducting a PET examination. Thus, it is possible to shorten total examination time required for radiological imaging of a PET examination and an X-ray computed tomographic examination. Like JP-A-7-20245, particularly when the X-ray computed tomographic examination and the PET examination are continuously performed and the X-ray computed tomographic examination is performed more than once, after the first X-ray computed tomographic examination and the first PET examination are completed, the following operations are carried out: when the first PET examination is completed, application of voltage to the radiation detector (referred to as a radiation detector A) of the PET imaging apparatus is stopped, and the bed is moved to bring the examination range of the examinee 35 to the position of the X-ray computed tomography imaging apparatus. Thereafter, voltage is applied to the radiation detector of the X-ray computed tomography apparatus (referred to as a radiation detector B), and the X-ray computed tomographic examination is carried out. When the X-ray computed tomographic examination is completed, application of voltage to the radiation detector B is stopped, and the bed is moved to bring the examination range of the examinee 35 to the position of the X-ray computed tomography imaging apparatus. Thereafter, once again, voltage is applied to the radiation detector A to perform a PET examination. When the PET examination is completed, application of voltage to the radiation detector A is stopped. Thereafter, the above operations are repeated as necessary. As described above, in the radiological imaging of JP-A-7-20245, movement of the bed, application of voltage to the radiation detector, and stopping of the application need to be performed for several times in accordance with the number of times of the X-ray computed tomographic examinations. Thus, it takes a long time to complete the radiological imaging.

(2) In this embodiment, since the X-ray computed tomographic examination is performed in a part of the radiological imaging examination period, radiation dose applied to the examinee 35 by irradiation of X-rays is equal to or less than permissible exposure.

(3) The radiation detector 4 which has detected γ-rays is used as the radiation detector 4 for detecting X-rays. Thus, in the radiation imaging apparatus 1, it is not necessary to separately provide the radiation detector 4 for detecting X-rays and the radiation detector 4 which has detected γ-rays, and therefore the configuration can be simpler and smaller. The radiation detector 4 outputs both of the X-ray detection signal and the γ-ray detection signal.

(4) Since the X-ray computed tomographic examination is performed more than once during the radiological imaging examination period, even when the examinee 35 moves during the radiological imaging examination period, it is possible to obtain an X-ray detection signal after the movement. Therefore, based on the γ-ray detection signal during the radiological imaging examination period and the X-ray detection signals detected by two or more X-ray computed tomographic examinations performed in the radiological imaging examination period, it is possible to obtain an accurate tomographic image (including images of an affected area, bones, and internal organs) of the examinee 35 even when the examinee 35 moves. Namely, since the movement of the examinee 35 affects an X-ray computed tomographic image and a PET image, which will be discussed later, it is possible to obtain an accurate combined tomographic image using the affected images as will be discussed later.

(5) In this embodiment, the radiation detector 4 which has detected γ-rays is used as the radiation detector 4 for detecting X-rays (X-rays for obtaining an X-ray detection signal are detected using the radiation detector 4 which detects γ-rays for obtaining a γ-ray detection signal). Thus, in this embodiment, it is possible to reconstruct a first tomographic image (X-ray computed tomographic image) at a position of an affected area (PET radiopharmaceutical concentrates thereon) including an image of internal organs, bones, and so on of the examinee 35 by using an X-ray detection signal, which is one output signal of the radiation detectors 4 placed like a ring, and to reconstruct a second tomographic image (PET image) including an image of the affected area of the examinee 35 using a γ-ray detection signal, which is another output signal of the radiation detector 4. Data of the first tomographic image and data of the second tomographic image are reconstructed based on the output signals of the radiation detectors 4 for detecting both of transmitted X-rays and γ-rays. Thus, it is possible to accurately align and combine the data of the first tomographic image and the data of the second tomographic image at the position of an affected area. For this reason, it is possible to readily obtain an accurate tomographic image (combined tomographic image) including the affected area, internal organs, and bones. With such a combined tomographic image, it is possible to accurately identify the position of the affected area based on the internal organs and bones. For example, it is possible to readily obtain image data including the combined tomographic images by aligning the data of the first tomographic image data and the data of the second tomographic image centered on the axial center of the through hole section 30 of the image pickup apparatus 2.

(6) In this embodiment, the X-ray detecting section detects X-rays irradiated from the X-ray source 9 and passing through an affected area of the examinee 35, and the γ-ray detecting section detects γ-rays emitted by radiopharmaceutical from a part (affected area) where X-rays are transmitted in the body of the examinee 35 at the position where X-rays are irradiated to the examinee 35. Hence, it is possible to perform the X-ray computed tomographic examination and the PET examination at the same position without moving the examinee 35 using the bed 16. During the examinations, the X-ray detecting section outputs a detection signal of an X-ray passing through the affected area of the examinee 35 and the γ-ray detecting section outputs a detection signal of a γ-ray emitted from the affected area. To combine the first tomographic image data obtained from the X-ray detection signals at the position of the affected area and the second tomographic image data obtained from γ-ray detection signals at position of the affected area, even when the examinee 35 cannot help moving on the bed 16 during the examinations, the pieces of tomographic image data can be combined with accuracy. Namely, it is possible to obtain combined tomographic image data with accuracy. Hence, it is possible to improve accuracy of diagnosis on an affected area using combined tomographic image data (combined tomographic image) at the affected area displayed on the display device 29. Particularly, even when an affected area exists on a part having internal organs arranged in a complicated manner, the combined tomographic image obtained by this embodiment makes it possible to properly find the position of an affected area, thereby improving accuracy of diagnosis on an affected area.

(7) In this embodiment, the X-ray source 9 can be moved in the axial direction of the radiation detecting section 65 during radiological imaging using an X-ray source axial transfer apparatus (e.g., the axial transfer arm 11). Hence, without moving the examinee 35 in the axial direction of the radiation detecting section 65, it is possible to perform the X-ray computed tomographic examination on an examination range while performing the PET examination thereon. When the X-ray computed tomographic examination on the examination range is performed by moving the bed 16 instead of moving the X-ray source 9 in the axial direction, a part where PET radiopharmaceutical concentrates also moves in the axial direction. Thus, a position for generating γ-ray pairs moves in the axial direction and noise for producing PET image data is increased, so that accurate PET image data cannot be obtained. In this embodiment, since a position for generating γ-ray pairs does not move in the axial direction, it is possible to obtain accurate PET image data, thereby improving accuracy of combined tomographic image data.

(8) In this embodiment, it is possible to detect a plurality of γ-ray pairs emitted from the examinee 35 by the radiation detectors 4 included in the radiation detecting section 65 and it is also possible to detect X-rays emitted from the X-ray source 9 and passing through the examinee 35, the X-ray source 9 moving in the circumferential direction. Although the conventional art requires an image pickup apparatus for detecting X-rays and another image pickup apparatus for detecting γ-rays, this embodiment merely requires a single image pickup apparatus for detecting X-rays and γ-rays, thereby simplifying the configuration of the radiological imaging apparatus for performing both of the X-ray computed tomographic examination and the PET examination.

(9) This embodiment can obtain X-ray detection signals necessary to create a first tomographic image and γ-ray detection signals necessary to create a second tomographic image from the shared radiation detectors 4, and can thereby shorten the time required to examine the examinee 35 (examination time) significantly. In other words, this embodiment can obtain X-ray detection signals necessary to create a first tomographic image and γ-ray detection signals necessary to create a second tomographic image in a short examination time. This embodiment eliminates the need to move the examinee from one image pickup apparatus for detecting penetrating X-rays to another image pickup apparatus for detecting γ-rays as in the case of the conventional art, and can further contribute to shortening the time for examining the examinee.

(10) This embodiment rotates the X-ray source 9 and does not move the radiation detecting section 65 in the circumferential direction and axial direction of the through hole section 30, and can thereby reduce the capacity of the motor for rotating the X-ray source 9 compared to the motor for moving the radiation detecting section 65. It is also possible to reduce power consumption required to drive the motor of the latter compared to that of the motor of the former.

(11) Since the number of γ-ray detection signals inputted to the X-ray detection signal processor 22, that is, the first signal processor is reduced significantly, it is possible to obtain exact first tomographic image data. Thus, using image data obtained by combining the first tomographic image data and second tomographic image data, it is possible to know the position of the affected area precisely.

(12) In this embodiment, the X-ray source 9 rotates inside the radiation detecting section 65, and therefore the diameter of the ring-shaped holding section 5 increases and the number of radiation detectors 4 that can be placed in the circumferential direction inside the ring-shaped holding section 5 can be increased. This increase in the number of radiation detectors 4 in the circumferential direction results in an improvement of sensitivity and resolution, thereby improving resolution on the cross section of the examinee 35.

(13) In this embodiment, since the axial transfer arm 11 to which the X-ray source 9 is attached and the X-ray source 9 are positioned inside the radiation detectors 4, there is a possibility that they will block γ-rays emitted from the examinee 35, preventing the radiation detectors 4 located right behind them from detecting γ-rays, and losing detection data necessary to create a PET image. However, since the X-ray source 9 and axial transfer arm 11 are rotated in the circumferential direction by the X-ray source drive 10 in this embodiment as described above, loss of data is practically not a problem. Especially, the rotational speed of the X-ray source 9 and axial transfer arm 11 is approximately 1 sec/slice, and therefore it is sufficiently short when compared to a time required for a PET examination which is on the order of a few minutes at a minimum. Loss of data is therefore practically no problem from this aspect, too. Furthermore, when X-ray computed tomographic examination is not performed but PET examination is performed, since the X-ray source 9 is housed in the X-ray source drive 10, the X-ray source 9 and the axial transfer arm 11 does not interfere with detection of γ-rays.

Furthermore, the time required to examine an X-ray detection signal to create an X-ray computed tomographic image is shorter than the time required to obtain a γ-ray image detection signal to create a PET image. Thus, by always irradiating the examinee with X-rays from the X-ray source 9 and obtaining an X-ray detection signal during an examination time to obtain a γ-ray detection signal, it is possible to correct deviations of PET image data due to movements of the examinee from continuous X-ray computed tomographic images obtained based on the X-ray detection signal even if the examinee moves during the examination.

In Embodiment 1, the control function of the general controller 47 may be performed using a program in the computer 27. In this case, the computer 27 having the control function is substantially an apparatus in which a tomographic image data generator and the general controller 47 are integrated with each other.

Although irradiation of X-rays is performed in the form of fan beams in Embodiment 1, the irradiation is not limited to the above. For example, X-rays may be irradiated in the form of cone beams to obtain three-dimensional combined tomographic image data. Although a semiconductor radiation detector using CdTe is employed as the radiation detector 4 in Embodiment 1, a semiconductor radiation detector using CZT and GaAs is also applicable. Further, it is also possible to use a scintillator, which is a radiation detector other than the semiconductor radiation detector. Although the X-ray source or the X-ray source and the radiation detector are rotated around the examinee in Embodiment 1, the X-ray source and the radiation detector may be fixed and the examinee may be rotated around them.

In Embodiment 1, an examination on the examinee in the axial direction of the hole 30 is performed by moving the bed 16. Meanwhile, the examination may be performed by moving the image pickup apparatus in the axial direction while the bed 16 is fixed. Further, the arrangement of the radiation detectors is not limited to a cylindrical form. For example, a polygonal cylinder such as a hexagon is also applicable.

When the position of an affected area of the examinee 35 is not identified in advance, the bed 16 is moved to perform the PET examination over the body of the examinee 35. During the PET examination, the X-ray source 9 is rotated in the circumferential direction and an X-ray computed tomographic examination is performed on a part undergoing the PET examination.

As shown in FIG. 6, the X-ray computed tomographic examination is performed for four times in Embodiment 1. When the examinee can be perfectly fixed or when an examination range is small and the PET examination is completed in a short time, the number of times of the X-ray computed tomographic examination may be one.

Figure 10:
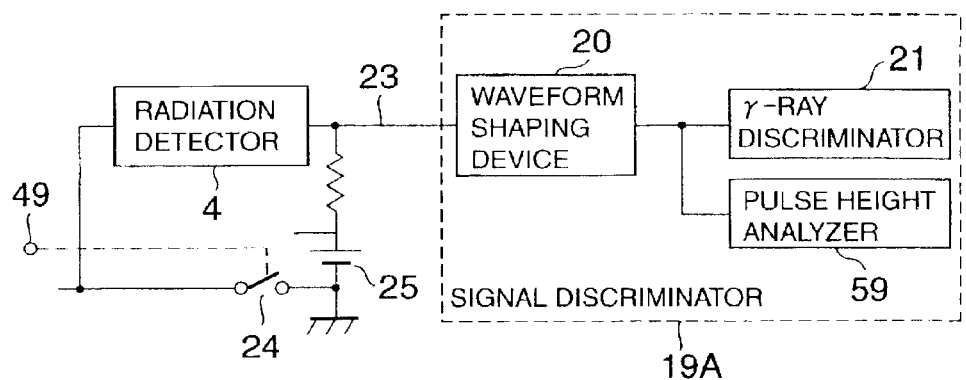
FIG. 10 is a structural diagram showing another embodiment of a signal discriminator.

In Embodiment 1, a signal discriminator 19A of FIG. 10 may be used instead of the signal discriminator 19 of FIG. 4. As shown in FIG. 10, the signal discriminator 19A comprises a waveform shaping device 20, a γ-ray discriminator 21, and a pulse height analyzer 58. The signal discriminator 21 provided for each of the radiation detectors 4 does not have the changeover switch 31, and the waveform shaping device 20 is connected to the corresponding radiation detector 4 via the wiring 23. The pulse height analyzer 59 is connected to the waveform shaping device 20 and the computer 27. The γ-ray discriminator 21 connected to the waveform shaping device 20 is connected to the coincidence counter 26. The pulse height analyzer 59 is an X-ray detection signal processor.

When the signal discriminator 19A is used, the X-ray emission control section 51 outputs a shutter opening signal in response to input of an X-ray computed tomographic examination start signal and outputs a shutter closing signal in response to input of an X-ray computed tomographic examination end signal. Thus, during the X-ray computed tomographic examination, the shutter 44 is always opened when X-rays are emitted, and the radiation detector 4 detects γ-rays as well as X-rays. The signal discriminator 19A has the function of separating X-ray detection signals and γ-ray detection signals from output signals of the radiation detector 4. Namely, the signal discriminator 19A is an apparatus for performing energy discrimination on an X-ray detection signal and a γ-ray detection signal that are outputted from one of the radiation detectors 4. The waveform shaping device 20 shapes X-ray detection signals as well as γ-ray detection signals to a Gaussian distribution and outputs the signals. γ-ray detection signals and X-ray detection signals which are the output of the waveform shaping device 20 are inputted to the γ-ray discriminator 21 and the pulse height analyzer 59. The γ-ray discriminator 21 needs to process γ-ray detection signals and the pulse height analyzer 59 needs to process X-ray detection signals. The γ-ray discriminator 21 has the same function as the γ-ray discriminator 21 of the signal discriminator 19. The energy of X-rays irradiated to the examinee 35 is 80 keV. The pulse height analyzer 59 outputs an integrated value for each set period of an X-ray detection signal, that is, information on intensity of X-rays when an X-ray detection signal having energy ranging from the second energy set value (70 keV) to the third energy set value (90 keV) is inputted from the waveform shaping device 20. The load of the pulse height analyzer 59 is remarkably reduced by processing on an X-ray detection signal having such a specific energy.

(Embodiment 2)

Figure 11:
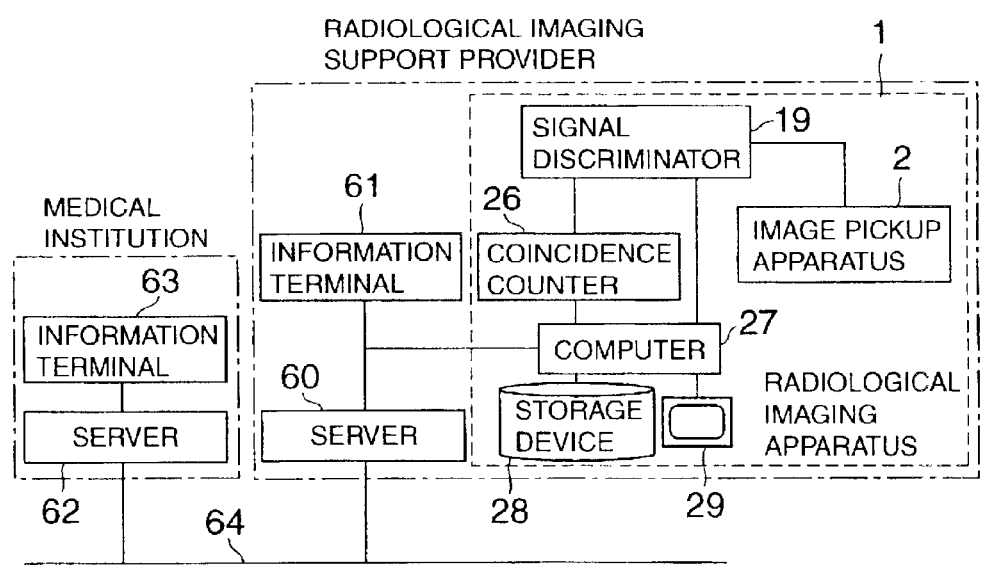
FIG. 11 is a structural diagram showing a transmittance system of tomographic image data used for a radiological imaging support method of Embodiment 2, which is another embodiment of the present invention.

Referring to FIG. 11, the following will discuss a radiological imaging support method using the radiological imaging apparatus 1 shown in FIG. 1. In hospitals as medical institutions, names of examinees undergoing radiological imaging are inputted every day to an information terminal 63, and the names are transmitted to a server 60 of a radiological imaging support provider via a server 62 and a communication line 64 of the hospital when radiological imaging is requested to the radiological imaging support provider. The transmitted examination dates and names of the examinees on each radiological imaging date are displayed on a display device of the information terminal 61 of the radiological imaging support provider. The radiological imaging apparatus 1 owned by the radiological imaging support provider for examinations is installed in the hospital. PET radiopharmaceutical is administered to an examinee 35 in the hospital. A radiologic technologist who is an employee of the radiological imaging support provider lays the examinee 35 administered with the radiopharmaceutical on a bed 16. When the radiologic technologist presses a button switch

54, as described in Embodiment 1, under control of a general controller 47, radiological imaging is performed on the corresponding examinee 35 using the radiological imaging apparatus 1, that is, a PET examination and an X-ray computed tomographic examination are performed. The radiological imaging makes it possible to a γ-ray detection signal and an X-ray detection signal that are the output from the radiation detector 4 as discussed in Embodiment 1. Information obtained by the processing is inputted to a computer 27, the processing of FIG. 9 is performed, and combined tomographic data is generated. The combined tomographic image data is outputted together with the name information of the examinees to the server 60 from the computer 27, and the image data is inputted to the information terminal 63 of the hospital requesting examinations via the communication line 64 and the server 62 and is displayed on the display device. Doctors of the hospital perform diagnostics on an affected area while observing the displayed combined tomography. Since the radiological imaging apparatus 1 is used to perform the radiological imaging, the effects (1) to (13) of the embodiment can be achieved. Particularly in this embodiment, as described above, an X-ray computed tomographic examination is performed when a PET examination is performed in radiological imaging examination period. Thus, it is possible to provide an accurate tomographic image including an affected area and bones to the hospital. Doctors of the hospital can properly perform diagnostics on an affected area based on the tomographic image. This radiological imaging support method also means that radiological imaging is performed on parts where at least some detecting positions of X-rays and some detecting positions of γ-rays are the same (at least some of a plurality of radiation detectors 4 are shared and some of the radiation detectors 4 output both of X-ray and γ-ray detection signals).

In this embodiment, instead of the radiological imaging apparatus 1, it is also possible to use any one of radiological imaging apparatuses 1A, 1B, 1C, and 1D which will be discussed later.

(Embodiment 3)

Figure 12:
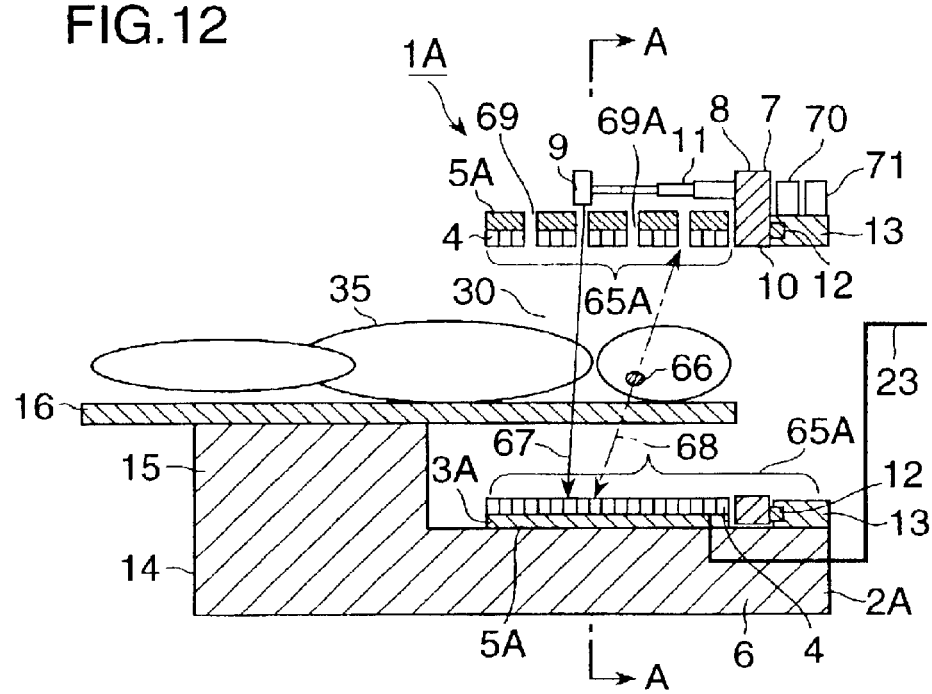
FIG. 12 is a longitudinal sectional view showing a radiological imaging apparatus according to Embodiment 3, which is a preferred embodiment of the present invention.
Figure 13:
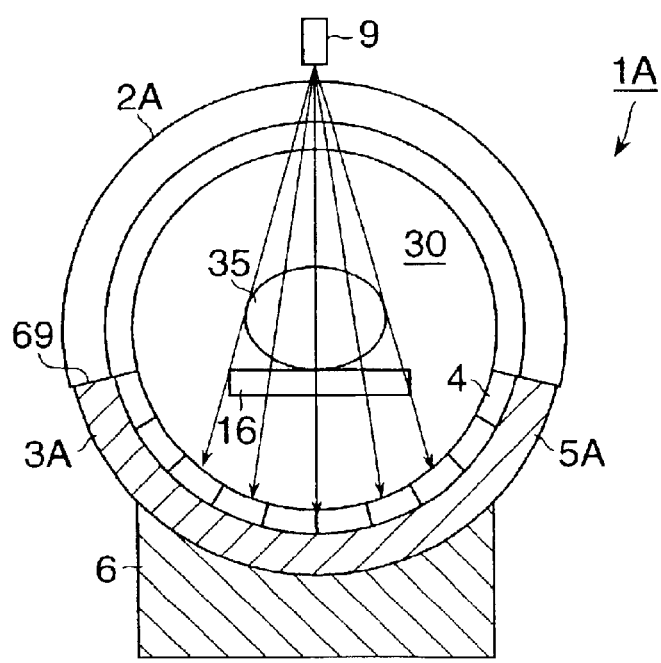
FIG. 13 is a sectional view taken along a line A—A of FIG. 12.

Referring to FIGS. 12 and 13, the following will discuss a radiological imaging apparatus of Embodiment 3, which is another embodiment of the present invention. A radiological imaging apparatus 1A of this embodiment comprises an image pickup apparatus 2A and an examinee holding apparatus 14 and further comprises a signal discriminator 19, a coincidence counter 26, a computer 27, a storage device 28, and a display device 29 (not shown) that are discussed in Embodiment 1. The configuration of the examinee holding apparatus 14 of this embodiment is identical to that of Embodiment 1.

The image pickup apparatus 2A is placed in a direction perpendicular to the longitudinal direction of the bed 16 and has a radiation detector ring 3A, an X-ray source circumferential transfer device 7, a drive controller 70, and an X-ray source controller 71. The radiation detector ring 3A includes a ring-shaped holding section 5A and a number of radiation detectors 4 aligned like a ring inside the ring-shaped holding section 5A. As shown in FIGS. 12 and 13, a plurality of semicircular slits 69 which are formed as gaps is provided in the axial direction on the radiation detector ring 3A. To be specific, the slits 69 are formed on the ring-shaped holding section 5A. Except for the slits 69, a number of radiation detectors (semiconductor radiation detectors) are placed inside the ring-shaped holding section 5A as in the case of Embodiment 1. A number of radiation detectors 4 included in the radiation detector ring 3A constitute a radiation detecting section 65A. The ring-shaped holding section 5A is placed on a supporting member 6. The image pickup apparatus 2A which has the γ-ray detecting section and the X-ray detecting section is a radiation detecting device too. The radiation detecting section 65A has the γ-ray detecting section and the X-ray detecting section.

The X-ray source circumferential transfer device 7 of this embodiment is identical in configuration to that of Embodiment 1. An X-ray source drive 10 of an X-ray source apparatus 8 (not shown in FIG. 12) comprises motors 17 and 18 (see FIG. 1). In this embodiment, the X-ray source 9 and an axial transfer arm 18 is placed outside the radiation detecting section 65A, to be specific, outside the radiation detector ring 3A. The drive controller 70 and the X-ray source controller 71 are placed on the outer surface of the ring-shaped holding section 5A. This embodiment is another example for performing an X-ray computed tomographic examination and a PET examination using one image pickup apparatus 2A.

Before radiological imaging is performed, like Embodiment 1, the examinee 35 is administered with PET radiopharmaceutical beforehand by means of injection so that radioactivity doses into the body are 370 MBq or less. The examinee 35 waits for a predetermined time until the PET radiopharmaceutical is spread inside the body to make image taking possible and concentrated on an affected area 66. After the lapse of the predetermined time, the examinee 35 is laid down on the bed 16 of an examinee holding apparatus 14. X-ray computed tomographic examination and PET examination of this embodiment are conducted by moving the bed 16 on which the examinee 35 is laid down and with the examinee 35 inserted in a through hole section 30 and using the image pickup apparatus 2A.

The X-ray source controller 71 controls time of emitting X-rays from the X-ray source 9. Namely, during an X-ray computed tomographic examination, the X-ray source controller 71 repeats the following control: an X-ray generation signal is outputted to close a switch 57 (see FIG. 1) provided between an anode (or cathode) of an X-ray tube 42 and a power supply in the X-ray source 9, an X-ray stop signal is outputted to open the switch 57 after the lapse of a first set time, and the switch 57 is closed after the lapse of a second set time. Voltage is applied between the anode and cathode during the first set time and voltage is not applied during the second set time. This control allows pulse-like X-rays 67 to be emitted from the X-ray tube 42. The X-ray source 9 of this embodiment does not have a shutter 44 unlike Embodiment 1. As in the case of Embodiment 1, irradiation time T serving as the first set time is set at, for example, 1 μsec so that the probability that the first radiation detectors 4 detect γ-rays is negligible. The second set time is a time $T_0$ during which the X-ray source 9 moves between one radiation detector 4 and another radiation detector 4 adjacent thereto and is determined by the moving speed of the X-ray source 9 in the circumferential direction of the guide rails 12. The first and second set times are stored in the X-ray source controller 71.

The X-ray source 9 is attached diagonally such that the X-rays 67 emitted from the X-ray source 9 pass through slits 69 to the radiation detector 4 which is adjacent to the radiation detector 4 opposed to the slit 69 in the axial direction of a through hole section 30. The slits 69 are X-ray openings for permitting X-rays to pass through. When an X-ray computed tomographic examination is started, the drive controller 70 outputs a drive start signal to close a first switch (not shown) connected to the motor 17 and to a power supply. The motor 17 is rotated by supplying current, its rotational force is transmitted to a pinion via a power transmission mechanism, and the pinion is rotated. Since the pinion is engaged with a rack of the guide rail 12, the X-ray source apparatus 8, that is, the X-ray source 9 moves along the guide rail 12 in the circumferential direction. The X-ray source 9 moves at a set speed around the radiation detector ring 3A. When the X-ray computed tomographic examination is completed, the drive controller 70 outputs a drive stop signal to open the first switch. Thus, the movement of the X-ray source 9 in the circumferential direction is stopped. The slits 69 are placed in a semicircle and the X-ray source 9 is moved within this range. In this embodiment, a radiation detector 65A does not move in the circumferential direction or in the axial direction of the through hole section 30. A control signal is transmitted from the immobile X-ray source controller 71 and drive controller 70 to a mobile X-ray source 8 using a publicly known technology that will not interfere with the movement of the X-ray source 8.

The drive start signal outputted from the drive controller 70 when starting an X-ray computed tomographic examination is inputted to the X-ray source controller 71. The X-ray source controller 71 outputs an X-ray generation signal based on the input of the drive start signal. Then, X-ray source controller 71 outputs X-ray stop signals and X-ray generation signals repeatedly. By repeatedly outputting X-ray stop signals and X-ray generation signals, the X-ray source 9 emits X-rays for a first set time, that is, 1 μsec and stops the emission of X-rays for a second set time. This emission and stop of emission of X-rays are repeated during a period of circumferential movement of the X-ray source 9. The X-rays 67 emitted from the X-ray source 9 are irradiated in the form of fan beams through the slits 69 onto the examinee 35 inserted in the through hole section 30. As the X-ray source 9 moves in the circumferential direction, the examinee 35 on the bed 16 is irradiated with X-rays 67 from all directions. These X-rays 67 pass through the examinee 35 and are detected by a plurality of radiation detectors 4 placed in the circumferential direction centered on the radiation detector 4 which is located at 180° from the slit 69 with the axial center of the through hole section 30 as the base point. These first radiation detectors 4 output X-ray detection signals. These X-ray detection signals are input to their respective signal discriminators 19 through their respective wirings 23.

The movement of the X-ray source 9 in the circumferential direction is completed within the range of the slit 69 at the position of the slit 69 where the X-rays 67 pass through as shown in FIG. 12. After the X-ray computed tomographic examination is completed at the slit 69, the drive controller 70 closes the second switch (not shown) connected to the motor 18 of the X-ray source drive 10 and the power supply. Thus, the motor 18 is driven to cause the axial transfer arm 11 to contract, and the X-ray source 9 is moved to the position of a slit 69A. Emission of the X-rays 67 from the X-ray source 9 is stopped by the action of the X-ray source controller 71 when the axial transfer arm 11 spreads and contracts.

When the X-ray source 9 reaches the position of the slit 69A, the X-ray source controller 71 emits the X-rays 67 from the X-ray source 9. The X-rays 67 pass through the slit 69A and an affected area 66 opposed to the slit 69A. The X-rays 67 passing through the affected area 66 are detected by the radiation detector 4.

511 keV γ-rays 68 caused by PET radiopharmaceutical are emitted from the affected area 66 of the examinee 35 on the bed 16 inserted into the through hole section 30. The radiation detectors (second radiation detectors) 4 other than the first radiation detectors 4 detect the γ-rays 68 and output detection signals of the γ-rays 68. These γ-ray detection signals are entered to their respective signal discriminators 19 through the respective wirings 23.

The changeover operation of a switch 31 in the signal discriminator 19 is controlled by the drive controller 70. The drive controller 70 performs the same control as that of the changeover switch control section 52 of Embodiment 1 and switches connection of a movable terminal 32 to a fixed terminal 33 or a fixed terminal 34. When the drive controller 70 selects another radiation detector 4 because of a movement of the X-ray source 9 in the circumferential direction, the movable terminal 32 connected to the radiation detector 4 serving as a newly selected first radiation detector 4 is connected to the fixed terminal 34. The movable terminal 32 connected to the radiation detector 4 serving as a deselected first radiation detector 4 is connected to the fixed terminal 33 by the drive controller 70 in accordance with the movement of the X-ray source 9 in the circumferential direction.

Like Embodiment 1, in this embodiment, each of the radiation detectors 4 in the radiation detecting section 65A serves as the first radiation detector 4 at one time and serves as the second radiation detector 4 at another time in accordance with the position of the X-ray source 9. Thus, one radiation detector 4 outputs both of the X-ray detection signal and a γ-ray detection signal at different times. The probability of detection of the γ-rays 68 from the examinee 35 by the first radiation detector 4 during the first set time of 1 μsec is as small as negligible as described above.

When the position of the affected area 66 of the examinee 35 is not identified in advance, a PET examination is performed on each range permitting one PET examination (length in the axial direction of the radiation detecting section 65A) over the body of the examinee 35. In each PET examination, the X-ray source 9 is rotated in the circumferential direction, and an X-ray computed tomographic examination is performed on each point where the PET examination is performed. When the position of the affected area 66 of the examinee 35 is identified by another examination in advance, the bed 16 is moved to insert the affected area 66 identified beforehand into the through hole section 30, and the PET examination and X-ray computed tomographic examination are performed around the affected area using an image pickup apparatus 2A.

X-ray pickup and γ-ray detection signal outputted from the radiation detector 4 are processed in the signal discriminator 19 as in the case of Embodiment 1. The coincidence counter 26 is fed a pulse signal from the γ-ray discriminator 21 of each signal discriminator 19, and performs the same processing as that of Embodiment 1. The computer 27 performs the processing of the steps 36 to 41 shown in FIG. 9, which was discussed in Embodiment 1, obtains combined tomographic image data in cross section at the position of the affected area 66 of the examinee 35, and displays the combined tomographic image data on the display device 29.

In this embodiment as well, in radiological imaging period for obtaining a detection signal of a γ-ray 78 required to create tomographic image data of the examinee 35, the PET examination for detecting the γ-rays 68 emitted from the affected area 66 and the X-ray computed tomographic examination for detecting the X-rays 67 passing through the examinee 35 are performed. The time required for the X-ray computed tomographic examination is shorter than time required for the PET examination. The X-ray computed tomographic examination of this embodiment is started as follows: an X-ray computed tomographic examination start signal of the drive controller 70 is inputted when an operator such as a radiologic technologist presses a button for starting the X-ray computed tomographic examination on an operating panel (not shown), and the drive controller 70 outputs the above drive start signal. As shown in FIG. 6, two or more times of X-ray computed tomographic examinations may be performed in one radiation detection period in this embodiment as well.

In this embodiment, two-dimensional sectional data on one cross section of the examinee 35 can be obtained by moving the X-ray source 9 in the circumferential direction and using a detection signal of the X-ray 67 passing through one of the slits 69. Two-dimensional sectional data on one cross section of the examinee 35 can be obtained by stretching the axial transfer arm 11 and moving the X-ray source 9 to the position of another slit 69. Three-dimensional sectional data can be obtained by accumulating these two-dimensional sectional data pieces.

According to this embodiment, the effects (1) to (11) can be achieved. This embodiment can further achieve effects (14) and (15) discussed below.

(14) In this embodiment, the X-ray source 9 rotates outside the cylindrical radiation detecting section 65A, and therefore the diameter of the radiation detecting section decreases in diameter. A pair of γ-rays emitted in disappearance of protons are emitted in a direction of 180°±0.6°. Thus, when the radiation detecting section decreases in diameter, an error decreases, thereby improving image resolution. Further, the number of radiation detectors 4 can be reduced.

(15) In this embodiment, since the axial transfer arm 11 to which the X-ray source 9 is attached and the X-ray source 9 are placed outside the radiation detectors 4, there is no possibility that they block γ-rays emitted from the examinee 35, prevent the radiation detectors 4 located right behind them from detecting γ-rays, and lose detection data necessary to create a PET image.

(Embodiment 4)

Figure 14:
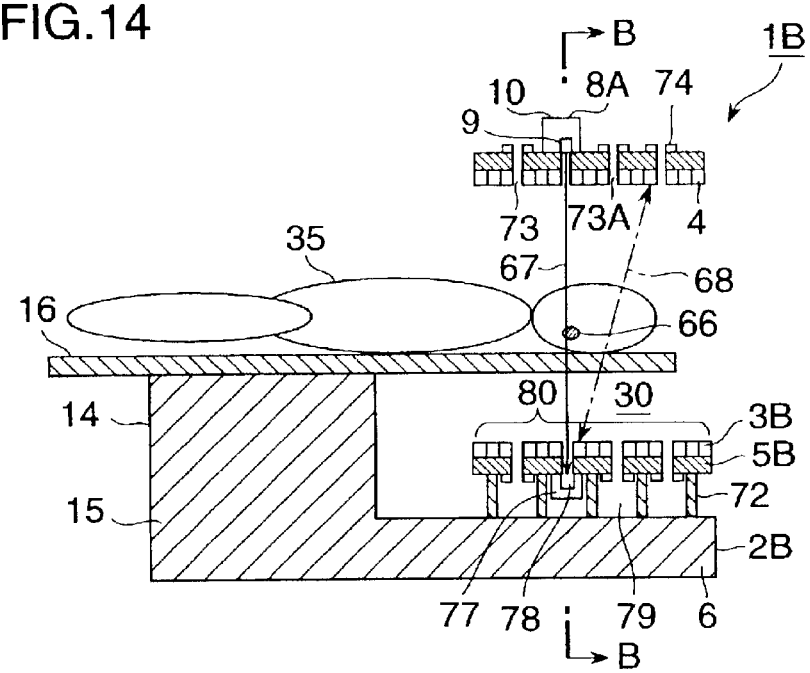
FIG. 14 is a longitudinal sectional view showing a radiological imaging apparatus according to Embodiment 4, which is another embodiment of the present invention.
Figure 15:
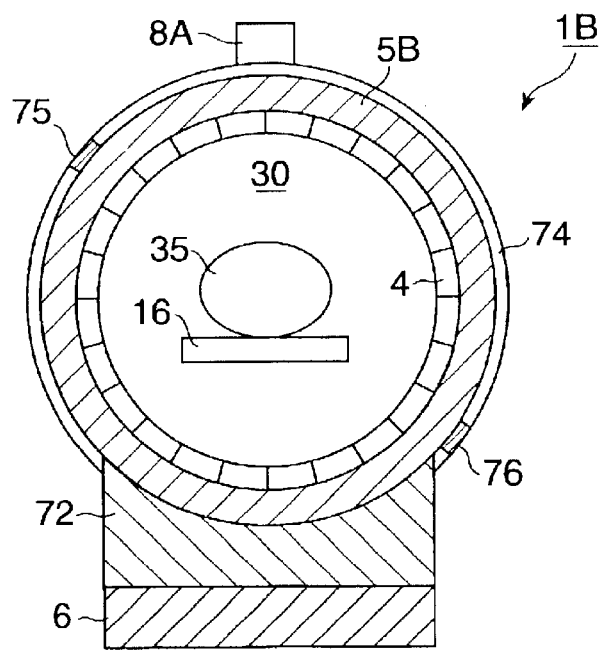
FIG. 15 is a sectional view taken along line B—B of FIG. 14.

Referring to FIGS. 14 and 15, the following will discuss a radiological imaging apparatus according to Embodiment 4, which is another embodiment of the present invention. A radiological imaging apparatus 1B of this embodiment comprises an image pickup apparatus 2B and an examinee holding apparatus 14 and further comprises a γ-ray discriminator 21 of FIG. 10, a coincidence counter 26 of Embodiment 1, a computer 27, a storage device 28, and a display 29 (not shown in FIG. 14). Since a difference from Embodiment 3 lies in the image pickup apparatus 2B, the image pickup apparatus 2B will be mainly discussed below.

The image pickup apparatus 2B comprises a plurality of radiation detector rings 3B, an X-ray source apparatus 8A, an X-ray detecting device 77, a detector holding apparatuses 72, circumferential guide rails 74, an X-ray source axial guide rail 75, and a detector axial guide rail 76.

The plurality of radiation detector rings 3B are separately placed in parallel by the detector holding apparatuses 72 on a supporting member 6. The radiation detector rings 3B have a plurality of radiation detectors 4 placed in the circumferential direction and the axial direction on the inner surfaces of ring-shaped holding sections 5B. The ring-shaped holding sections 5B are attached to the detector holding apparatuses 72. Gaps 73 are formed between the radiation detector rings 3B. The ring-shaped circumferential guide rails 74 are placed on the outer surfaces of the ring-shaped holding sections 5B. The X-ray source axial guide rail 75 and the detector axial guide rail 76 are placed 180° away from each other in the axial direction on the outer surfaces of the ring-shaped holding sections 5B.

The X-ray source apparatus 8A has an X-ray source drive 10 and an X-ray source 9 placed on the X-ray source drive 10. The X-ray source drive 10 has a motor, a reduction gear mechanism, and two kinds of pinions for circumferential movement and axial movement (not shown) in its casing. When the X-ray source apparatus 8A moves in the circumferential direction, the reduction gear mechanism is connected to the pinion for the circumferential movement to transfer driving force obtained by rotation of the motor to the pinion for the circumferential movement. When the X-ray source apparatus 8A moves in the axial direction, the reduction gear mechanism is connected to the pinion for the axial movement to transfer driving force obtained by rotation of the motor to the pinion for the axial movement. Since the pinion for circumferential movement engages with a rack provided on the circumferential guide rail 74 and since the pinion for axial movement engages with a rack provided on the guide rail 75, the self-propelled X-ray source apparatus 8A can move in all directions on the outer surfaces of the ring-shaped holding sections 5B. The X-ray source 9 is placed in the X-ray source apparatus 8A in such a manner as to face the ring-shaped holding section 5B.

The X-ray detecting device 77 is connected to the X-ray source apparatus 8A outside the ring-shaped holding sections 5B via semicircular connecting members (not shown). Thus, when the X-ray source apparatus 8A moves along the circumferential guide rail 74 in the circumferential direction of the ring-shaped holding section 5B, the X-ray detecting device 77 is moved outside the ring-shaped holding part 5B along the circumferential guide rail 74 in the circumferential direction of the ring-shaped holding section 5B by the movement of the X-ray source apparatus 8A. When the X-ray source apparatus 8A moves along the X-ray source axial guide rail 75 in the axial direction of the ring-shaped holding section 5B, the X-ray detecting device 77 is moved outside the ring-shaped holding part 5B along the detector guide rail 76 in the axial direction of the ring-shaped holding section 5B by the movement of the X-ray source apparatus 8A. The X-ray detecting device 77 has a plurality of X-ray detectors 78 in the circumferential direction of the through hole section 30. The plurality of X-ray detectors 78 constitutes an X-ray detecting section. The plurality of X-ray detectors 78 may be arranged also in the axial direction of the ring-shaped holding section 5B.

A cylindrical γ-ray detecting section 80 is constituted by the radiation detectors 4 provided on all of the radiation detector rings 3B. The X-ray detecting section is positioned in a region formed between one end and the other end of the γ-ray detecting section 80 in the longitudinal direction of the bed 16. The radiation detector 4 and the X-ray detector 78 are semiconductor radiation detectors described in Embodiment 1. In this embodiment, the X-ray source 9 is placed outside the radiation detector rings 3B, that is, the γ-ray detecting section 80.

Unlike Embodiments 1 and 3 where the X-ray detecting section and the γ-ray detecting section are integrated, the X-ray detecting section and the γ-ray detecting section are separately provided in this embodiment. The configuration where the X-ray detecting section and the γ-ray detecting section are separated is also applied to Embodiments 5 and 6, which will be discussed later. The image pickup apparatus 2B which has the γ-ray detecting section and the X-ray detecting section is a radiation detecting device too.

The examinee 35 administered with PET radiopharmaceutical is moved to a predetermined position in the through hole section 30 by moving the bed 16. When an operator such as a radiologic technologist presses an X-ray computed tomographic examination start button on an operating panel (not shown), an X-ray computed tomographic examination start signal is inputted to a drive controller (not shown) and an X-ray source controller (not shown), and an X-ray computed tomographic examination of this embodiment is started. The X-ray source controller fed with the X-ray computed tomographic examination start signal closes a switch 57 (see FIG. 1). Hence, X-rays 67 are emitted from the X-ray source 9. The X-rays 67 emitted from the X-ray source 9 are irradiated onto the examinee 35 through the gap 73. The control of the drive controller rotates the motor, and the X-ray source apparatus 8A is moved along the circumferential guide rail 74. The X-ray source apparatus 8A and the X-ray detector 77 are moved and rotated in a space 79 formed between the adjacent detector holding apparatuses 72. Hence, the X-rays 67 emitted from the X-ray source 9 are irradiated onto the examinee 35 from all directions. The X-rays 67 passing through the examinee 35 are detected by the X-ray detectors 78 of the X-ray detecting section. To move the X-ray source apparatus 8A and the X-ray detector 77 to an adjacent gap 73 (e.g., a gap 73A), after irradiation of the X-rays 67 to the examinee 35 through one gap 73 is completed, the X-ray source apparatus 8A is moved along the X-ray source axial guide rail 75. At this moment, the X-ray detector 77 moves along the detector axial guide rail 76. When the X-ray source apparatus 8A moves along the X-ray source axial guide rail 75, since the switch 57 is opened by the control of the X-ray source controller, X-rays are not emitted from the X-ray source 9. When the X-ray source apparatus 8A reaches the adjacent gap 73A, the X-ray source apparatus 8A and the X-ray detector 77 are moved along the circumferential guide rail 74. At this moment, the X-rays 67 are emitted from the X-ray source 9 by the action of the X-ray source controller. The X-rays 67 are emitted to an affected area 66 of the examinee 35 through the gap 73A. The X-rays 67 passing through the affected area 66 are detected by the X-ray detectors 78. The X-ray computed tomographic examination is completed when the X-ray source apparatus 8A reaches a predetermined position at the completion of the X-ray computed tomographic examination.

The radiation detectors 4 of the γ-ray detecting section 80 detect γ-rays 68 emitted from the affected area 66. A γ-ray detection signal outputted from the radiation detector 4 is inputted to a γ-ray discriminator 21 via a waveform shaping device 20. The γ-ray discriminator 21 performs the same processing as Embodiment 1 to output a pulse signal. A coincidence counter 26 is fed a pulse signal outputted from the γ-ray discriminator 21 of each signal discriminator 19, and performs the same processing as Embodiment 1. An X-ray detection signal outputted from the X-ray detector 78 is processed by a signal processor (not shown). The signal processor outputs information on intensity of an X-ray that is an integrated value of the X-ray detection signals. The computer 27 for inputting the information on the intensity of the X-ray performs processing of steps 36 to 41 shown in FIG. 9 as discussed in Embodiment 1, calculates combined tomographic image data in cross section on the affected area 66 of the examinee 35, and displays the combined tomographic image data on a display device 29.

In this embodiment as well, a PET examination for detecting the γ-rays 68 emitted from the affected area 66 and an X-ray computed tomographic examination for detecting the X-rays 67 passing through the examinee 35 are performed in a radiological imaging examination period for obtaining detection signals of the γ-rays 68 required to create tomography image data of the examinee 35. In this embodiment as well, the X-ray computed tomographic examination may be performed more than once during one radiological imaging period.

According to this embodiment, the effects (1), (2), (4), (6), (7), (10), (11), (14), and (15) of Embodiment 3 can be achieved. Furthermore, the following effects can be achieved.

(16) In this embodiment, since the X-ray detecting section (to be specific, the X-ray detector 78) is placed between one end and the other end of the γ-ray detecting section 80 in the axial direction, on a predetermined region of the examinee 35 undergoing the PET examination, the X-ray computed tomographic examination can be performed at the same position without moving the examinee 35 from the bed 16. Thus, even when the examinee 35 moves on the bed 16, it is possible to accurately combine first tomographic image data and second tomographic image data on the affected area. For example, it is possible to easily combine the first tomographic image data and the second tomographic image data by aligning the image data centered on the axial center of the through hole section 30 of the image pickup apparatus 2B. Therefore, particularly even when an affected area exists on a part where internal organs are arranged in a complicated manner, a tomographic image obtained by this embodiment makes it possible to properly find the position of the affected area, thereby improving accuracy of diagnosis on an affected area.

(17) This embodiment can eliminate the need for a changeover switch 31 used in Embodiment 1. Namely, the radiation detector 4 placed on the ring-shaped holding section 5B is connected to the γ-ray discriminator 21 via wiring 23 and the waveform shaping device 20. Meanwhile, the X-ray detectors 78 are directly connected to the signal processor via wiring (not shown). Therefore, the circuit configuration can be simplified. Further, it is possible to eliminate the need for the control of the changeover switch and so on, thereby simplifying the controlling method.

(18) In this embodiment, the X-ray source apparatus 8A and the X-ray detecting device 77 can rotate by 360°. Hence, in the X-ray computed tomographic examination, it is possible to obtain data in the direction of 360° to obtain one tomographic image, thereby improving picture quality of an X-ray tomographic image.

(19) In this embodiment, the X-ray source apparatus 8A and the X-ray detecting device 77 are opposed to each other with respect to the central axis of the through hole section 30. Therefore, when a two-dimensional sectional image is taken, it is possible to irradiate X-rays in parallel with the cross section, thereby improving picture quality of an X-ray computed tomographic image.

(20) In this embodiment, X-rays can be irradiated in parallel with the gap 73. Therefore, it is possible to minimize the width of the gap 73 to a width substantially equal to a beam width. The gap 73 is a region losing data when the PET examination is performed. By minimizing the width of the gap 73, it is possible to increase the speed and improve picture quality in the PET examination.

(21) In this embodiment, the X-ray detecting device 77 is provided separately from the radiation detector 4 which detects γ-rays for PET examination. Therefore, it is possible to arbitrarily set an array pitch of the X-ray detectors 78 in the X-ray detecting device 77, thereby readily increase resolution of an X-ray computed tomography image.

(Embodiment 5)

Figure 16:
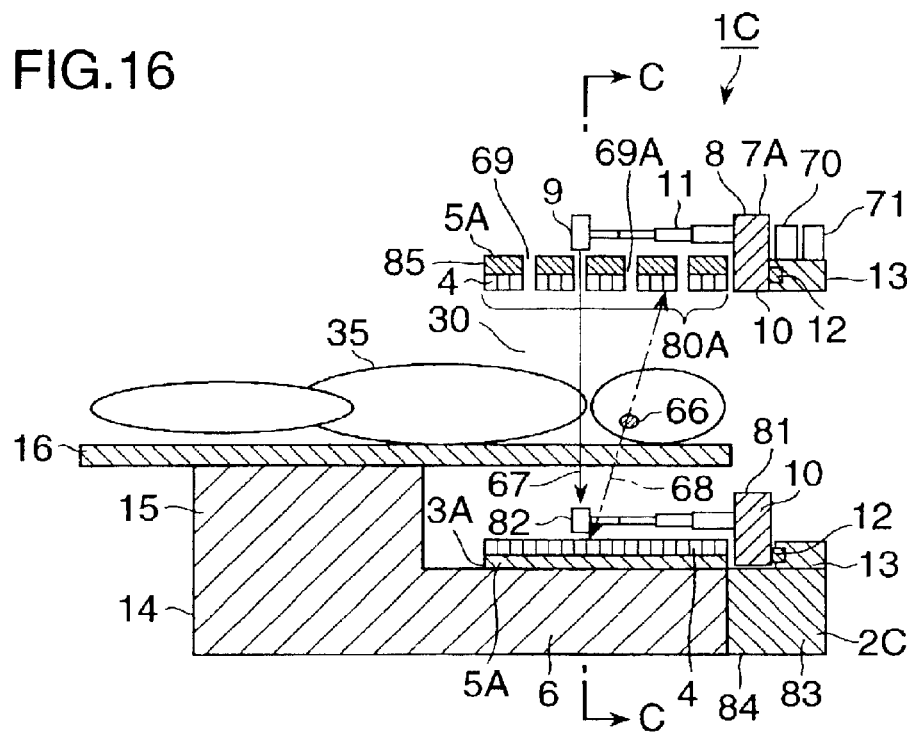
FIG. 16 is a longitudinal sectional view showing a radiological imaging apparatus according to Embodiment 5, which is another embodiment of the present invention.
Figure 17:
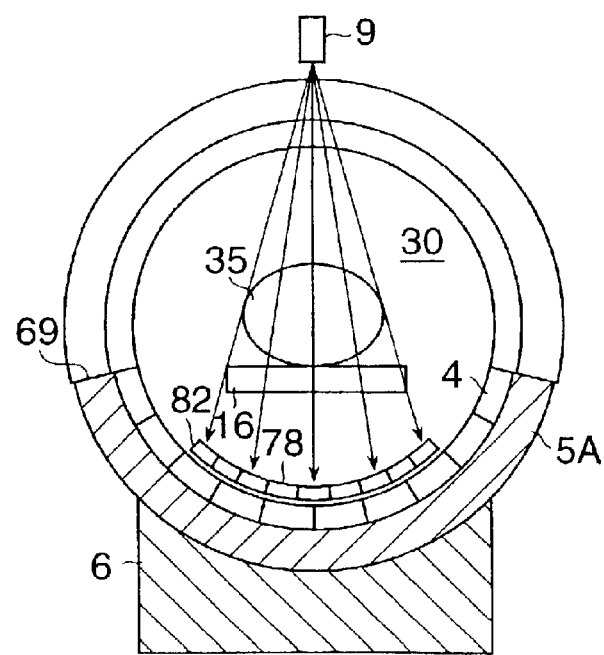
FIG. 17 is a sectional view taken along a line C—C of FIG. 16.

Referring to FIGS. 16 and 17, the following will discuss a radiological imaging apparatus according to Embodiment 5, which is another embodiment of the present invention. A radiological imaging apparatus 1C of this embodiment comprises an image pickup apparatus 2C and an examinee holding apparatus 14 and further comprises a γ-ray discriminator 21 of FIG. 10, a coincidence counter 26 of Embodiment 1, a computer 27, a storage device 28, and a display device 29 (not shown in FIG. 16). The image pickup apparatus 2C which has the γ-ray detecting section and the X-ray detecting section is a radiation detecting device too.

The image pickup apparatus 2C of this embodiment is configured such that an axial expansion arm 81 and an X-ray detecting section 82 are added to the image pickup apparatus 2A. However, an X-ray source apparatus holding apparatus 13 is placed on a supporting member 83 which is detachably attached to a supporting member 6. The axial expansion arm 81 is attached to the casing of an X-ray source drive 10 at a position 180° opposite to the axial expansion arm 11. The X-ray detecting section 82 is placed on the leading end of the axial expansion arm 81 and comprises a plurality of X-ray detectors 78 in the circumferential direction of a through hole section 30 as shown in FIG. 17. An X-ray source circumferential transfer apparatus 7A of this embodiment has an X-ray source 9, the X-ray source drive 10, the X-ray source apparatus holding apparatus 13, the axial expansion arms 11 and 81, and the X-ray detecting section 82. A plurality of radiation detectors 4 arranged like a cylinder constitutes a γ-ray detecting section 80A. The expansion of the axial expansion arm 81 is performed by driving a motor 18 as in the case of the axial expansion arm 11. Another configuration of the image pickup apparatus 2C is identical to that of the image pickup apparatus 2A. Besides, the image pickup apparatus 2C has an X-ray image pickup apparatus 84 and a γ-ray image pickup apparatus 85. The X-ray image pickup apparatus 84 has the X-ray source circumferential transfer apparatus 7A, a drive controller 70, an X-ray source controller 71, and the supporting member 83. The γ-ray image pickup apparatus 85 has a radiation detector ring 3A and the supporting member 6.

By moving the X-ray source drive 10 along the guide rail 12, the X-ray source 9, the axial expansion arm 11, the X-ray detecting section 82, and the axial expansion arm 81 moves around the examinee 35 on the bed 16 in the range of a circumferential length of the slit 69 as in the case of Embodiment 3. The X-rays 67 emitted from the X-ray source 9 are irradiated to, for example, the examinee 35 administered with PET radiopharmaceutical through slits 69A, and pass through the affected area 66. The X-rays 67 passing through the affected area 66 are detected by the X-ray detector 78 of the X-ray detecting section 82. By moving the axial expansion arms 11 and 81, the X-ray source 9 and the X-ray detecting section 82 are moved in the axial direction of the through hole section 30 while being opposed to each other. The γ-rays 68 emitted from the affected area 66 by the PET pharmaceutical are detected by the radiation detectors 4 of the γ-ray detecting section 80A.

An X-ray detection signal outputted from the X-ray detector 78 and a γ-ray detection signal outputted from the radiation detector 4 are processed as with Embodiment 4. This processing makes it possible to obtain combined tomographic image data in cross section at the position of the affected area 66 of the examinee 35, and the combined tomographic image data is displayed on the display device 29.

According to this embodiment, the effects (1), (2), (4), (6), (7), (10), (11), (14) to (17) and (19) to (21) of Embodiment 4 can be achieved. This embodiment can further achieve the following effects.

(22) In this embodiment, the X-ray source 9 and the X-ray detecting section 82 are attached to the X-ray source drive 10 in such a manner as to be opposed to each other, and an X-ray examination can be performed by movement of the X-ray drive device 10 in the circumferential direction. Therefore, during an X-ray computed tomographic examination, it is possible to simultaneously control the movement of the X-ray source 9 and the X-ray detecting section 82 in the circumferential direction of the through hole section 30, thereby simplifying the controlling method.

(23) In this embodiment, the X-ray image pickup apparatus 84 is detachable. When the device 84 is detached, an X-ray computed tomographic examination can be separately performed using the X-ray image pickup apparatus 84.

(Embodiment 6)

Figure 18:
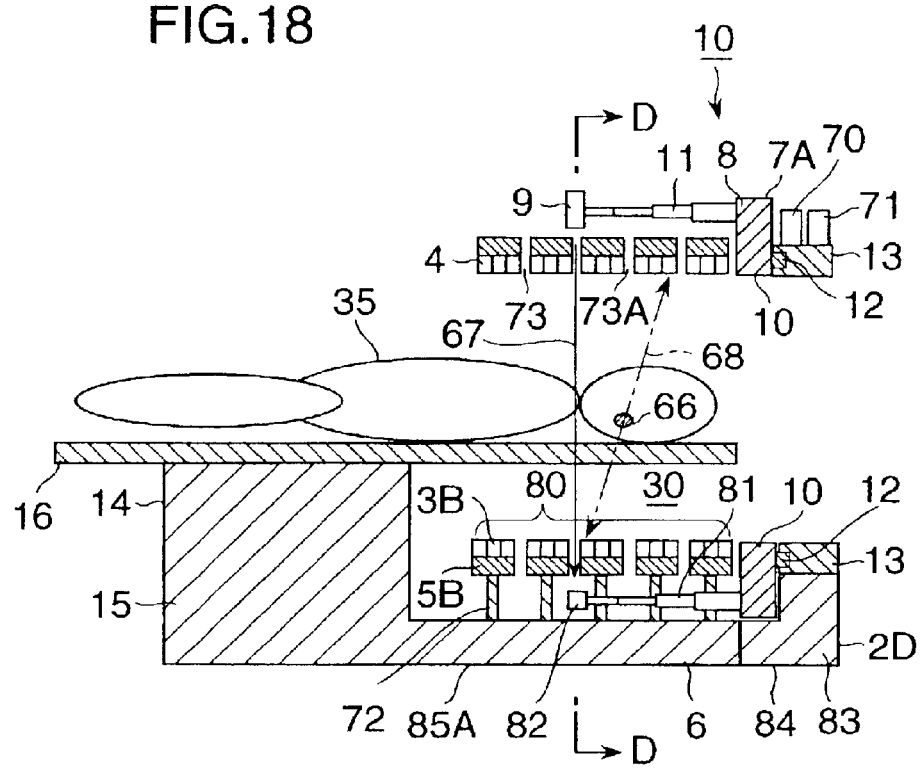
FIG. 18 is a longitudinal sectional view showing a radiological imaging apparatus according to Embodiment 6, which is another embodiment of the present invention.
Figure 19:
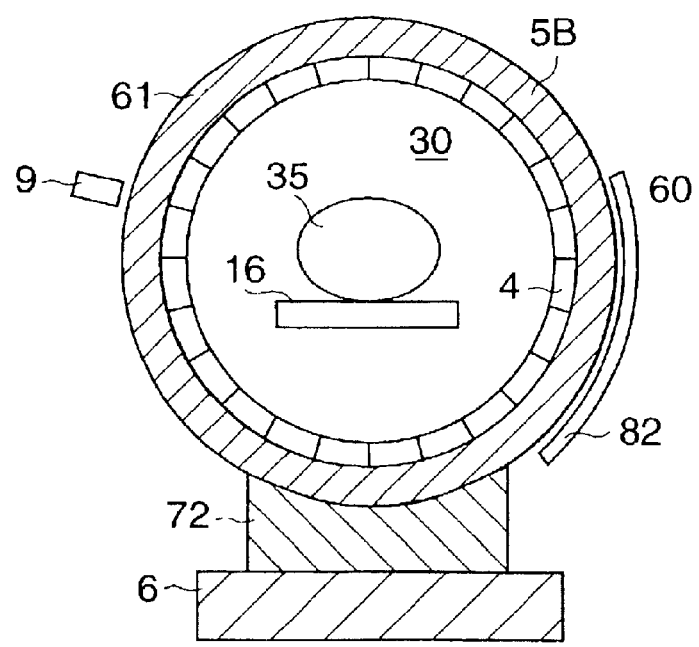
FIG. 19 is a sectional view taken along a line D—D of FIG. 18.

Referring to FIGS. 18 and 19, the following will discuss a radiological imaging apparatus according to Embodiment 6, which is another embodiment of the present invention. A radiological imaging apparatus 1D of this embodiment comprises an image pickup apparatus 2D and an examinee holding apparatus 14 and further comprises a γ-ray discriminator 21 of FIG. 10, a coincidence counter 26 of Embodiment 1, a computer 27, a storage device 28, and a display device 29 (not shown in FIG. 18). The image pickup apparatus 2D conceptually has an X-ray image pickup apparatus 84 (FIG. 16) of an image pickup apparatus 2C that is applied to an image pickup apparatus 2B (FIG. 14). Namely, the image pickup apparatus 2D comprises the X-ray image pickup apparatus 84 and a γ-ray image pickup apparatus 85A. The γ-ray image pickup apparatus 85A has a plurality of radiation detector rings 3B of Embodiment 4, a supporting member 6, and a ring-shaped holding member 72 for placing the radiation detector rings 3B on the supporting member 6. In this embodiment, the X-ray detecting section 82 and the axial expansion arm 81 are placed outside the radiation detector rings 3B. In this Embodiment, the X-ray source 9 and the X-ray detecting 82 can move in the circumferential direction of the through hole section 30 by the X-ray source drive 10 in a region other than the ring-shaped holding member 72. The X-ray detecting section 82 (not shown) has the same configuration as that of Embodiment 5. The image pickup apparatus 2D which has the γ-ray detecting section and the X-ray detecting section is a radiation detecting device too.

An X-ray detection signal outputted from the X-ray detector 78 and a γ-ray detection signal outputted from the radiation detector 4 are processed as with Embodiment 4. This processing makes it possible to obtain combined tomographic image data in cross section on the affected area 66 of the examinee 35, and the combined tomographic image data is displayed on the display device 29.

According to this embodiment, the effects (1), (2), (4), (6), (7), (10), (11), (14) to (17), and (19) to (23) of Embodiment 5 can be achieved. This embodiment makes it possible to reduce the diameter of the radiation detector ring as compared with Embodiment 5.

In embodiments 1-6, at least part of the X-ray detecting section may be positioned in a region formed between one end and the other end of a γ-ray detecting section in the longitudinal direction of a bed.

It should be further understood by those skilled in the art that although the foregoing description has been made on embodiments of the invention, the invention is not limited thereto and various changes and modifications may be made without departing from the spirit of the invention and the scope of the appended claims.

What is claimed is:

1. A radiological imaging apparatus, comprising:
   an X-ray source which is moved around a bed for supporting a test subject; and
   a radiation detecting device having a γ-ray detecting section for outputting detection signal of γ-rays, and an X-ray detecting section for outputting detection signals of X-rays
   wherein at least part of said X-ray detecting section is positioned in a region formed between one end and the other end of said γ-ray detecting section in the longitudinal direction of said bed; and
   said imaging apparatus further comprises an X-ray source transfer apparatus for moving said X-ray source in the longitudinal direction.

2. The radiological imaging apparatus according to claim 1, wherein said X-ray source is positioned in the region.

3. The radiological imaging apparatus according to claim 1, wherein said γ-ray detecting section and said X-ray detecting section are integrated to constitute a radiation detecting section serving as said γ-ray detecting section and said X-ray detecting section, and said radiation detecting section is constituted by said plurality of radiation detectors for outputting both of said γ-ray detection signal and said X-ray detection signal.

4. The radiological imaging apparatus according to claim 3, further comprising a first signal processor for inputting a detection signal of a γ-ray from said radiation detectors of said γ-ray detecting section and outputting first tomographic image information used for producing first tomographic image information including a part on which radiopharmaceutical concentrates, and a second image processor for inputting a detection signal of said X-ray from said radiation detectors of said X-ray detecting section and outputting second information used for producing second tomographic image information including bones, said second signal processor being provided for each of said radiation detectors of said X-ray detecting section.

5. The radiological imaging apparatus according to claim 1, wherein said γ-ray detecting section and said X-ray detecting section are separately provided.

6. The radiological imaging apparatus according to claim 1, further comprising a tomographic image producing apparatus for producing a tomographic image using first information obtained from said γ-ray detection signal and second information obtained from said X-ray detection signal.

7. The radiological imaging apparatus according to claim 1, further comprising:
   a first signal processing apparatus for inputting a detection signal of a γ-ray from radiation detectors of said γ-ray detecting section and outputting first information used for producing first tomographic image information including a part on which radiopharmaceutical concentrates; and
   a second signal processing apparatus for inputting a detection signal of said X-ray from said radiation detectors of said X-ray detecting section and outputting second information used for producing second tomographic image information including bones, said second signal processing apparatus being provided for each of radiation detectors of said X-ray detecting section.

8. The radiological imaging apparatus according to claim 7,
   wherein said first signal processing apparatus comprises:
   a γ-ray detection signal processor which inputs said γ-ray detection signal from said radiation detectors of said γ-ray detecting section and is provided for each of said radiation detectors; and
   a counter which inputs output signals from said γ-ray detection signal processors and outputs position information of a pair of said radiation detectors detecting the γ-rays in a set time and counter information of the detected γ-rays as said first information, and
   said radiological imaging apparatus further comprises a tomographic image producing apparatus for producing tomographic image information using said position information, said counter information, and said second information.

9. A radiological imaging apparatus according to claim 1, wherein said radiation detectors are semiconductor radiation detectors.

10. A radiological imaging apparatus, comprising:
    an X-ray source for moving around a bed to emit an X-ray;
    a γ-ray detecting section which is placed around said bed, detects a γ-ray, and outputs a detection signal of the γ-ray;
    an X-ray detecting section for detecting the X-ray and outputting a detection signal of the X-ray at a position on which the γ-ray is detected;
    a first X-ray source transfer apparatus for moving said X-ray source around said bed in a circumferential direction; and
    a second X-ray source transfer apparatus for moving said X-ray source in the longitudinal direction.

11. The radiological imaging apparatus according to claim 10, further comprising a tomographic image producing apparatus which produces first tomographic image information by using first information obtained from said γ-ray detection signal, second tomographic image information by using second information obtained from said X-ray detection signal, and third tomographic image information including said first tomographic image information and said second tomographic image information.

12. A radiological imaging apparatus, comprising:
    an X-ray source for irradiating an X-ray onto a test object;
    an X-ray detecting section for detecting an X-ray and outputting a detection signal of the X-ray, said X-ray being emitted from said X-ray source and passing through said test object;
    a γ-ray detecting section for detecting a γ-ray emitted from said examinee at a position of said test object irradiated with the X-ray and outputting a detection signal of the γ-ray; and
    an X-ray source transfer apparatus for moving said X-ray source in a longitudinal direction of a bed for supporting said test object.

13. A radiological imaging apparatus, comprising:
    a bed for placing a test object;
    a γ-ray detecting section in which a plurality of radiation detectors for detecting a γ-ray emitted from said test object are arranged;

an X-ray detecting section including a plurality of said radiation detectors for detecting an X-ray, at least a portion of said X-ray detection section being positioned in an area between one end and the other end of said γ-ray detecting section in a longitudinal direction of said bed;

an X-ray source for irradiating an X-ray onto said test object; and an X-ray source transfer apparatus for moving said X-ray source in said longitudinal direction of said bed, wherein said radiation detectors detect the X-ray passing through said test object; and said imaging apparatus further comprises signal processing apparatus for inputting a detection signal of the γ-ray and a detection signal of the X-ray, said signals being outputted from said radiation detectors.

14. A radiological imaging apparatus, comprising:

a bed for placing a test object;

a γ-ray detecting section which is placed substantially in parallel with the longitudinal direction of said bed and outputs a detection signal of a γ-ray;

an X-ray source positioned in a region formed between one end and the other end of said γ-ray detecting section in the longitudinal direction;

an X-ray detecting section for outputting a detection signal of an X-ray; and an X-ray source transfer apparatus for moving said X-ray source in said longitudinal direction of said bed.

15. A radiological imaging apparatus, comprising:

a bed for placing a test object;

a γ-ray detecting section which has a plurality of gaps placed substantially in parallel with the longitudinal direction of said bed at intervals in the longitudinal direction, and outputs a detection signal of a γ-ray;

an X-ray detecting section for outputting a detection signal of an X-ray;

an X-ray source for irradiating the X-ray onto said test object through said gaps; and an X-ray source transfer apparatus for moving said X-ray source in the longitudinal direction.

16. The radiological imaging apparatus according to claim 15, further comprising:

a first guide for guiding said X-ray source transfer apparatus in the longitudinal direction; and a second guide for guiding said X-ray source transfer apparatus in a direction perpendicular to the longitudinal direction around said bed.

17. The radiological imaging apparatus according to claim 15, wherein said γ-ray detecting section and said X-ray detecting section are integrated to constitute a radiation detecting section serving as said γ-ray detecting section and said X-ray detecting section, said radiation detecting section being constituted by a plurality of radiation detectors for outputting the γ-ray detection signal and the X-ray detection signal.

18. The radiological imaging apparatus according to claim 15, wherein said γ-ray detecting section is placed around said bed, and said X-ray detecting section is placed outside said γ-ray detecting section and detects the X-ray passing through said gaps formed on said γ-ray detecting section.

19. The radiological imaging apparatus according to claim 15, wherein said γ-ray detecting section is placed around said bed and said X-ray detecting section is placed inside said γ-ray detecting section.

20. The radiological imaging apparatus according to claim 15, wherein said radiation detectors constituting said γ-ray detecting section and said X-ray detecting section are semiconductor radiation detectors.

21. A radiological imaging apparatus, comprising:

a bed for placing a test object;

a γ-ray detecting device; and an X-ray detecting device detachably attached to said γ-ray detecting device, wherein said γ-ray detecting device has a γ-ray detecting section which is placed substantially in parallel with the longitudinal direction of said bed and outputs a detection signal of a γ-ray, and said X-ray detecting device has an X-ray detecting section for outputting a detection signal of an X-ray, an X-ray source for irradiating the X-ray onto said test object through gaps formed on said γ-ray detecting section, and an X-ray source transfer apparatus for moving said X-ray source in the longitudinal direction.

22. A radiological imaging apparatus, comprising:

a bed for placing a test object;

an image pickup apparatus; and a controller, wherein said image pickup apparatus has a plurality of first radiation detectors and includes a γ-ray detecting section positioned around said bed, an X-ray detecting section which has a plurality of second radiation detectors and outputs a detection signal of an X-ray, an X-ray source for emitting an X-ray to said test object, and first X-ray source transfer means for moving said X-ray source in the circumferential direction around said bed; and said imaging apparatus further comprises a first signal processor for inputting γ-ray detection signals from said first radiation detectors and outputting first information, a second processor for inputting X-ray detection signals from said second radiation detectors and outputting second information, and said controller performs control such that a plurality of radiation detectors and a power supply are connected to apply voltage to the plurality of radiation detectors, an X-ray is emitted from said X-ray source when a set time elapses from application of voltage to said radiation detectors, and said X-ray source emitting said X-ray is moved in the circumferential direction using said first X-ray source transfer apparatus.

23. The radiological imaging apparatus according to claim 22, wherein said radiation detectors are semiconductor radiation detectors.

24. The radiological imaging apparatus according to claim 22, wherein said γ-ray detecting section and said X-ray detecting section are integrated to constitute a radiation detecting section serving as said γ-ray detecting section and said X-ray detecting section, and said first and second radiation detectors constituting said radiation detecting section are a plurality of radiation detectors for outputting said γ-ray detection signal and said X-ray detection signal.

25. The radiological imaging apparatus according to claim 22, wherein said γ-ray detecting section and said X-ray detecting section are separately provided.

26. The radiological imaging apparatus according to claim 22, further comprising a tomographic image producing apparatus for producing first tomographic image information including an image on which radiopharmaceutical concentrates using said first information, producing second tomographic image information including an image of bones using said second information, and producing third tomographic image information including said first tomographic image information and said second tomographic image information.

27. A radiological imaging apparatus, comprising:
a bed for placing a test object;
a γ-ray detecting section for outputting a detection signal of a γ-ray, said γ-ray detecting section being arranged substantially in parallel with a longitudinal direction of said bed and placed so as to surround a circumference of said bed, and including a gap by which said γ-ray detecting section is divided into a plurality of blocks;
an X-ray detecting section for outputting a detection signal of an X-ray; and
an X-ray source for irradiating the X-ray onto said test object through said gap.

28. The radiological imaging apparatus according to claim 27, wherein said γ-ray detecting section comprises said gap formed in a circumferential direction of said γ-ray detecting section, and said radiological imaging apparatus further comprises an X-ray source transfer apparatus for moving said X-ray source in said circumferential direction along said gap.

29. The radiological imaging apparatus according to claim 28, wherein said X-ray detecting section is arranged at an outer side of said γ-ray detecting section and detects X-rays which have passed through said gap.

30. The radiological imaging apparatus according to claim 29, comprising a transfer apparatus for moving said X-ray source and said X-ray detecting section in said circumferential direction along said gap.

31. The radiological imaging apparatus according to claim 27, wherein said γ-ray detecting section and said X-ray detecting section are integrated to constitute a radiation detecting section serving as said γ-ray detecting section and said X-ray detecting section, and said radiation detecting section is constituted by said plurality of radiation detectors for outputting said γ-ray detection signal and said X-ray detection signal.

32. The radiological imaging apparatus according to claim 27, wherein said X-ray detecting section is arranged at an inner side of said γ-ray detecting section.

33. The radiological imaging apparatus according to claim 27, wherein each of said radiation detectors is a semiconductor radiation detector.

* * * * *